(12) United States Patent
Adachi et al.

(10) Patent No.: US 10,026,903 B2
(45) Date of Patent: Jul. 17, 2018

(54) COMPOUND HAVING SUBSTITUTED TRIPHENYLENE RING STRUCTURE, AND ORGANIC ELECTROLUMINESCENT DEVICE

(71) Applicants: Hodogaya Chemical Co., Ltd., Tokyo (JP); Kyushu University National University Corporation, Fukuoka-shi (JP)

(72) Inventors: Chihaya Adachi, Fukuoka (JP); Kazunori Togashi, Tokyo (JP); Norimasa Yokoyama, Tokyo (JP); Shintaro Nomura, Fukuoka (JP)

(73) Assignees: Hodogaya Chemical Co., Ltd., Tokyo (JP); Kyushu University, National University Corporation, Fukuoka-shi (JP)

( * ) Notice: Subject to any disclaimer, the term of this patent is extended or adjusted under 35 U.S.C. 154(b) by 0 days.

(21) Appl. No.: 15/604,075

(22) Filed: May 24, 2017

(65) Prior Publication Data

US 2017/0271595 A1    Sep. 21, 2017

Related U.S. Application Data

(62) Division of application No. 14/001,041, filed as application No. PCT/JP2012/001217 on Feb. 23, 2012, now Pat. No. 9,685,612.

(30) Foreign Application Priority Data

Feb. 23, 2011    (JP) .................................. 2011-037322

(51) Int. Cl.
*H01L 51/00* (2006.01)
*C07D 213/22* (2006.01)
(Continued)

(52) U.S. Cl.
CPC ........ *H01L 51/0054* (2013.01); *C07D 213/22* (2013.01); *C09K 11/06* (2013.01);
(Continued)

(58) Field of Classification Search
CPC ............. H01L 51/0067; H01L 51/0052; H01L 51/0072
See application file for complete search history.

(56) References Cited

U.S. PATENT DOCUMENTS

2009/0134780 A1*  5/2009  Ono ..................... C07D 213/22
                                                     313/504

FOREIGN PATENT DOCUMENTS

JP    2008-150365 A    7/2008
JP    2008-214306 A    9/2008
(Continued)

OTHER PUBLICATIONS

USPTO structure search, Aug. 2016.*
International Search Report dated Mar. 19, 2013, issued for PCT/JP2012/001217.
Office Action dated Jul. 1, 2014, issued for the Chinese patent application No. 201280010405.2 and Japanese translation thereof.

*Primary Examiner* — Gregory Listvoyb
(74) *Attorney, Agent, or Firm* — Locke Lord LLP; James E. Armstrong, IV; Nicholas J. DiCeglie, Jr.

(57) ABSTRACT

An organic compound having an excellent electron injection and transport performance is provided as a material for a low-power-consumption organic electroluminescent device. A low-power-consumption organic electroluminescent device is also provided by using the compound. The compound is a compound of general formula (1) or (2) having a substituted bipyridyl and triphenylene ring structure. The organic electroluminescent device includes a pair of electrodes, and one or more organic layers sandwiched between the pair of electrodes, and uses the compound as constituent material of at least one of the organic layers.

[Chemical Formula 1]

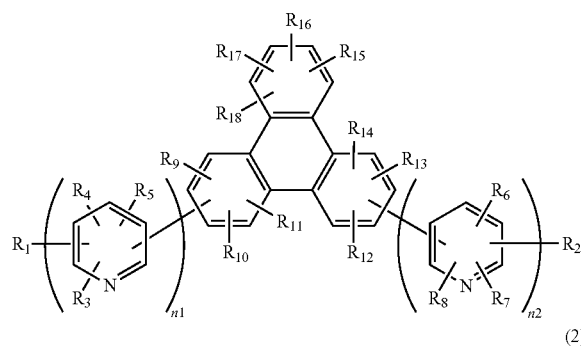

(1)

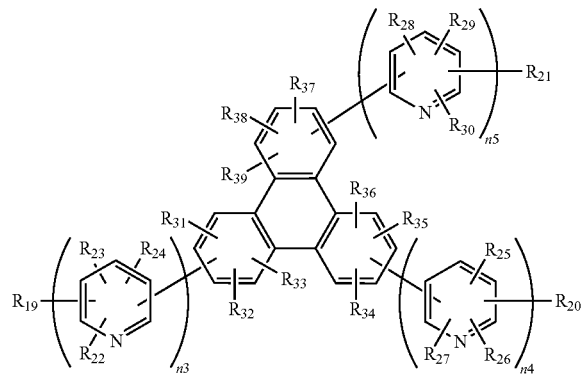

(2)

4 Claims, 5 Drawing Sheets

(51) Int. Cl.
*H05B 33/14* (2006.01)
*C09K 11/06* (2006.01)
*H01L 51/50* (2006.01)
*C07D 273/00* (2006.01)
*C07D 498/18* (2006.01)

(52) U.S. Cl.
CPC ...... *H01L 51/0058* (2013.01); *H01L 51/0059* (2013.01); *H01L 51/0067* (2013.01); *H05B 33/14* (2013.01); *C07D 273/00* (2013.01); *C07D 498/18* (2013.01); *C09K 2211/1425* (2013.01); *H01L 51/5012* (2013.01); *H01L 51/5072* (2013.01); *H01L 51/5092* (2013.01)

(56) References Cited

FOREIGN PATENT DOCUMENTS

| | | |
|---|---|---|
| JP | 2008-214307 A | 9/2008 |
| JP | 2008-247895 A | 10/2008 |
| TW | 200720253 A | 6/2007 |
| WO | WO-2007/029696 A1 | 3/2007 |

\* cited by examiner

← 7 CATHODE
← 6 ELECTRON INJECTION LAYER
← 5 ELECTRON TRANSPORT LAYER
← 4 LIGHT EMITTING LAYER
← 3 HOLE TRANSPORT LAYER
← 2 TRANSPARENT ANODE
← 1 GLASS SUBSTRATE

COMPOUND HAVING SUBSTITUTED TRIPHENYLENE RING STRUCTURE, AND ORGANIC ELECTROLUMINESCENT DEVICE

CROSS REFERENCE TO RELATED APPLICATIONS

This Application is a Division of U.S. patent application Ser. No. 14/001,041, filed on Oct. 17, 2013, which application is a 371 US National Phase Application of International PCT Patent Application No. PCT/JP2012/001217, filed on Feb. 23, 2012, which application claims priority to Japanese Patent Application No. JP 2011-037322, filed on Feb. 23, 2011. The entire contents of these applications are incorporated herein by reference in their entirety.

TECHNICAL FIELD

The present invention relates to compounds suited for an organic electroluminescent device (hereinafter, simply referred to as "organic EL device"), a preferred self light-emitting device for various display devices, and to the device. Specifically, the invention relates to compounds having a substituted bipyridyl and triphenylene ring structure, and to organic EL devices that use the compounds.

BACKGROUND ART

The organic EL device is a self-emitting device, and has been actively studied for their brighter, superior viewability and ability to display clearer images compared with the liquid crystal device.

In 1987, C. W. Tang et al. at Eastman Kodak developed a laminated structure device using materials assigned with different roles, realizing practical applications of an organic EL device with organic materials. These researchers laminated an electron-transporting phosphor and a hole-transporting organic material, and injected both the charges into the phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic EL device. In order to realize high efficiency and durability, various roles are further subdivided to provide an electroluminescent device that includes an anode, a hole injection layer, a hole transport layer, a light emitting layer, an electron transport layer, an electron injection layer, and a cathode successively formed on a substrate (refer to Non-Patent Document 1, for example).

Further, there have been attempts to use triplet excitons for further improvements of luminous efficiency, and use of phosphorescent materials has been investigated (refer to Non-Patent Document 2, for example).

The light emitting layer can also be fabricated by doping a charge-transporting compound, generally called a host material, with a phosphor or a phosphorescent material. As described in the foregoing Non-Patent Documents 1 and 2, selection of organic materials in an organic EL device greatly influences various device characteristics, including efficiency and durability.

In an organic EL device, the charges injected from both the electrodes recombine at the light emitting layer to cause emission. However, because the holes have greater mobility than the electrons, some of the holes pass through the light emitting layer, and lower efficiency. Accordingly, there is a need for an electron transport material that has high electron mobility.

Tris(8-hydroxyquinoline)aluminum (hereinafter, referred to simply as "Alq$_3$"), a representative light-emitting material, has been commonly used as an electron transport material. However, because of the slow electron mobility and the work function of 5.6 eV, it cannot be said that this material has a sufficient hole blocking performance.

One way of preventing some of the holes from passing through the light emitting layer and improving the probability of charge recombination at the light emitting layer is to insert a hole blocking layer. To date, various hole blocking materials have been proposed, including, for example, triazole derivatives (refer to Patent Document 3, for example), bathocuproin (hereinafter, referred to simply as "BCP"), and a mixed ligand complex of aluminum [aluminum(III)bis(2-methyl-8-quinolinate)-4-phenylphenolate (hereinafter, referred to simply as "BAlq")] (refer to Non-Patent Document 2, for example).

On the other hand, 3-(4-biphenylyl)-4-phenyl-5-(4-t-butylphenyl)-1,2,4-triazole (hereinafter, referred to simply as "TAZ") has been proposed as an electron transport material having an excellent hole blocking property (refer to Patent Document 3, for example).

TAZ has a large work function of 6.6 eV and a high hole blocking capability, and has been used as the electron-transporting hole blocking layer laminated on the cathode side of the fluorescent layer or phosphorescent layer produced by methods such as vacuum vapor deposition and coating. TAZ has contributed to improve the efficiency of organic EL devices (refer to Non-Patent Document 3, for example).

A major problem of TAZ, however, is the poor electron transporting property, and the material needs to be combined with an electron transport material of higher electron transporting property for the production of an organic EL device (refer to Non-Patent Document 4, for example).

BCP also has a large work function of 6.7 eV and a high hole blocking capability. However, because of the low glass transition point (Tg) of 83° C., the material has poor thin film stability, and cannot be said as being sufficiently functional as a hole blocking layer. In phosphorescent devices, it has been proposed to extend the device life by using BAlq as a hole blocking layer. While the device life can be extended by this approach, it is not possible to efficiently confine the holes in the light emitting layer because BAlq has only a small work function of 5.8 eV. The efficiency is thus inferior to a device using BCP, and it cannot be said that BAlq is satisfactory.

These materials all lack sufficient film stability, and are insufficient in terms of blocking holes. In order to improve the device characteristics of organic EL devices, organic compounds are needed that excel in electron injection and transport performance and hole blocking capability, and that has high stability in the thin-film state.

Improved compounds having an anthracene ring structure and a benzimidazole ring structure have been proposed (refer to Patent Document 4, for example).

However, devices using such compounds for the electron injection layer and/or the electron transport layer are still insufficient, even though luminous efficiency or the like is improved. Further improvements are thus needed to lower driving voltage, and increase luminous efficiency, particularly power efficiency.

CITATION LIST

Patent Documents

Patent Document 1: JP-A-8-048656
Patent Document 2: Japanese Patent No. 3194657
Patent Document 3: Japanese Patent No. 2734341
Patent Document 4: WO2003/060956

Non-Patent Documents

Non-Patent Document 1: The Japan Society of Applied Physics, 9th lecture preprints, pp. 55 to 61 (2001)
Non-Patent Document 2: The Japan Society of Applied Physics, 9th lecture preprints, pp. 23 to 31 (2001)
Non-Patent Document 3: The 50th Applied Physics-Associated Joint Lecture Presentation, 28p-A-6 Lecture Preprints, p. 1413 (2003)
Non-Patent Document 4: The Japan Society of Applied Physics, Molecular Electronics and Bioelectronics Journal, Vol. 11, 1, pp. 13 to 19 (2000)
Non-Patent Document 5: J. Org. Chem., 60, 7508 (1995)
Non-Patent Document 6: Synth. Commun., 11, 513 (1981)

SUMMARY OF THE INVENTION

Problems that the Invention is to Solve

It is an object of the present invention to provide organic compounds having an excellent electron injection and transport performance as material of low-power-consumption organic EL devices, and a low-power-consumption organic EL device that uses such compounds.

Some of the physical properties of the organic compounds to be provided by the present invention include (1) good electron injection characteristics, (2) fast electron mobility, (3) high molecular orientation, and (4) excellent heat resistance. Some of the physical properties of the organic EL device to be provided by the present invention include (1) high power efficiency, (2) low turn on voltage, and (3) low actual driving voltage.

Means for Solving the Problems

In order to achieve the foregoing object, the present inventors designed and chemically synthesized a compound by combining (i) a triphenylene ring structure having potential to provide desirable intermolecular packing in the thin-film state with its high planarity, and a desirable electron transport property with its abundant π electrons, and (ii) a bipyridyl group having high planarity and high electron affinity. The compound was used to fabricate various test organic EL devices, and device characteristics were evaluated to complete the present invention.

Specifically, the present invention is a compound of general formula (1) or (2) having a substituted bipyridyl and triphenylene ring structure.

[Chemical Formula 1]

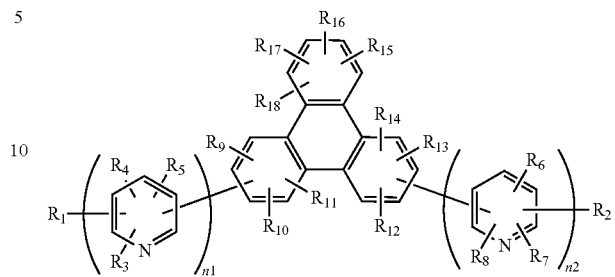

(1)

In the formula, $R_1$ to $R_{18}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group. n1 and n2 may be the same or different, and represent 2 or 3. The plurality of $R_3$ to $R_8$ may be the same or different, respectively.

[Chemical Formula 2]

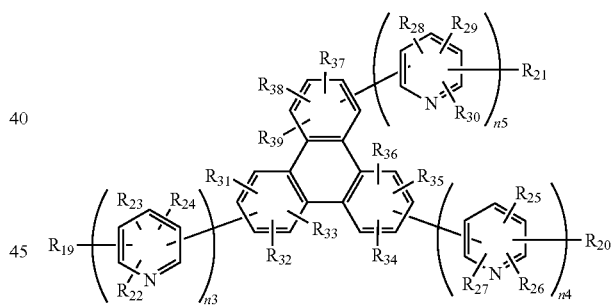

(2)

In the formula, $R_{19}$ to $R_{39}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group. n3, n4, and n5 may be the same or different, and represent 2 or 3. The plurality of $R_{22}$ to $R_{30}$ may be the same or different, respectively.

The present invention is a compound of the following general formula (1') having a substituted bipyridyl and triphenylene ring structure.

[Chemical Formula 3]

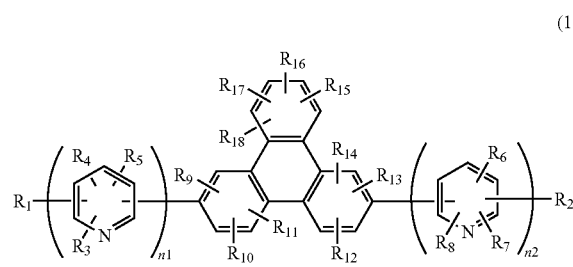

(1′)

In the formula, $R_1$ to $R_{18}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group. n1 and n2 may be the same or different, and represent 2 or 3. The plurality of $R_3$ to $R_8$ may be the same or different, respectively.

The present invention is a compound of the following general formula (1″) having a substituted bipyridyl and triphenylene ring structure.

[Chemical Formula 4]

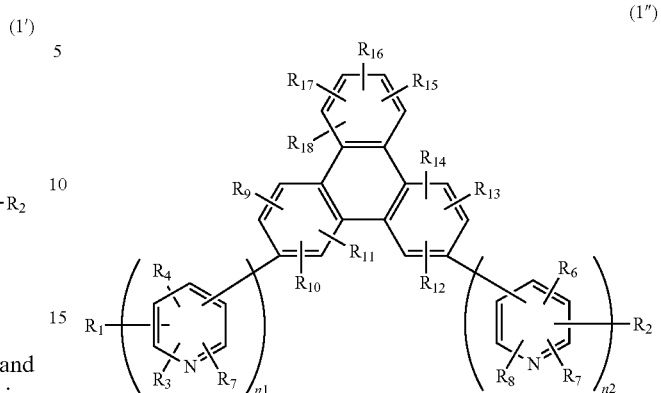

(1″)

In the formula, $R_1$ to $R_{18}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group. n1 and n2 may be the same or different, and represent 2 or 3. The plurality of $R_3$ to $R_8$ may be the same or different, respectively.

The present invention is a compound of the following general formula (1‴) having a substituted bipyridyl and triphenylene ring structure.

[Chemical Formula 5]

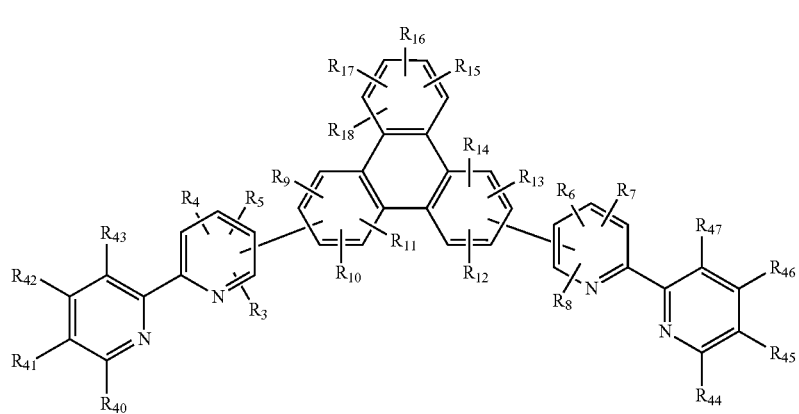

(1‴)

In the formula, $R_3$ to $R_{18}$, $R_{40}$ to $R_{47}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group.

The present invention is a compound of the following general formula (1″″) having a substituted bipyridyl and triphenylene ring structure.

[Chemical Formula 6]

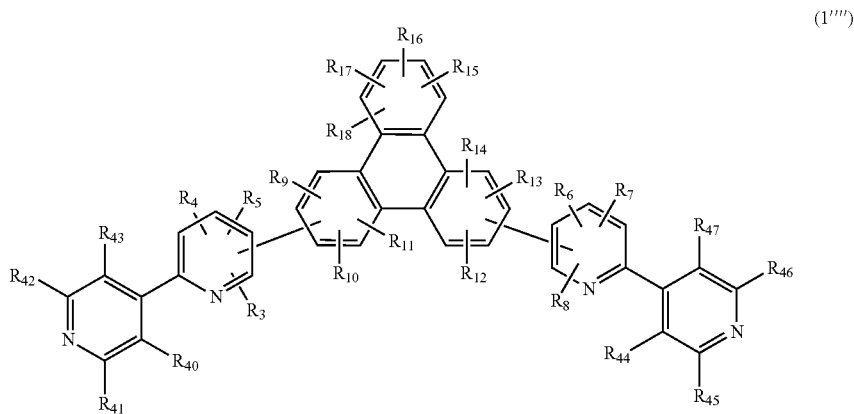

(1'''')

In the formula, $R_3$ to $R_{18}$, $R_{40}$ to $R_{47}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group.

The present invention is a compound of the following general formula (2') having a substituted bipyridyl and triphenylene ring structure.

[Chemical Formula 7]

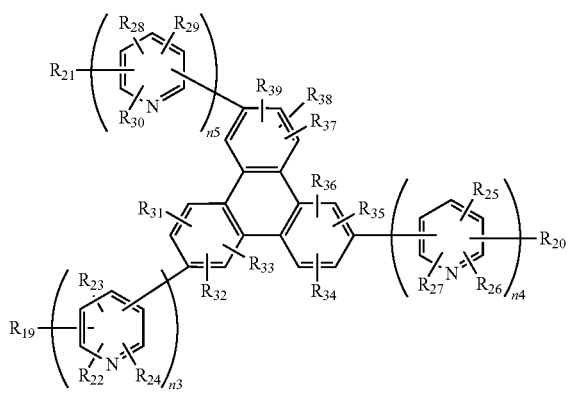

(2')

In the formula, $R_{19}$ to $R_{39}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group. n3, n4, and n5 may be the same or different, and represent 2 or 3. The plurality of $R_{22}$ to $R_{30}$ may be the same or different, respectively.

The present invention is an organic EL device that includes a pair of electrodes, and one or more organic layers sandwiched between the pair of electrodes, wherein at least one of the organic layers contains the compound of any of the general formulae (1) to (1''''), general formula (2), or general formula (2') having a substituted bipyridyl and triphenylene ring structure.

Specific examples of the "alkyl" in the "linear or branched alkyl of 1 to 6 carbon atoms that may have a substituent" represented by $R_1$ to $R_{47}$ in the general formulae (1) to (1''''), general formula (2), or general formula (2') include methyl, ethyl, n-propyl, isopropyl, n-butyl, isobutyl, tert-butyl, n-pentyl, isopentyl, neopentyl, and n-hexyl.

Specific examples of the "substituent" in the "substituted linear or branched alkyl of 1 to 6 carbon atoms" represented by $R_1$ to $R_{47}$ in the general formulae (1) to (1''''), general formula (2), or general formula (2') include a deuterium atom, a fluorine atom, a chlorine atom, cyano, nitro, linear or branched alkyl of 1 to 6 carbon atoms, cyclopentyl, cyclohexyl, dialkylamino substituted with linear or branched alkyl of 1 to 6 carbon atoms, phenyl, biphenylyl, terphenylyl, tetrakisphenyl, styryl, naphthyl, fluorenyl, phenanthryl, indenyl, pyrenyl, pyridyl, bipyridyl, triazyl, pyrimidyl, quinolyl, isoquinolyl, indolyl, pyridoindolyl, carbazolyl, quinoxalyl, and pyrazolyl. These substituents may be further substituted, and may be bound to each other to form a ring.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $R_1$ to $R_{47}$ in the general formulae (1) to (1''''), general formula (2), or general formula (2') include phenyl, biphenylyl, terphenylyl, tetrakisphenyl, styryl, naphthyl, anthryl, acenaphthenyl, fluorenyl, phenanthryl, indenyl, pyrenyl, pyridyl, bipyridyl, triazyl, pyrimidyl, furanyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, pyridoindolyl, dibenzofuranyl, dibenzothienyl, naphthyridinyl, phenanthrolinyl, and acridinyl.

Preferred as the "substituted or unsubstituted aromatic heterocyclic group" represented by $R_1$ to $R_8$, $R_{19}$ to $R_{27}$, and $R_{40}$ to $R_{47}$ is substituted or unsubstituted pyridyl, because it can be expected to improve the electron injection characteristics.

Specific examples of the "substituent" in the "substituted aromatic hydrocarbon group", "substituted aromatic heterocyclic group", or "substituted condensed polycyclic aromatic group" represented by $R_1$ to $R_{47}$ in the general formulae (1) to (1''''), general formula (2), or general formula (2') include a deuterium atom, a fluorine atom, a chlorine atom, cyano, trifluoromethyl, nitro, linear or branched alkyl of 1 to 6 carbon atoms, cyclopentyl, cyclohexyl, linear or branched alkoxy of 1 to 6 carbon atoms, dialkylamino substituted with linear or branched alkyl of 1 to 6 carbon atoms, phenyl, biphenylyl, terphenylyl, tetrakisphenyl, styryl, naphthyl, fluorenyl, phenanthryl, indenyl, pyrenyl, pyridyl, bipyridyl, triazyl, pyrimidyl, quinolyl, isoquinolyl, indolyl, pyridoindolyl, carbazolyl, quinoxalyl, and pyrazolyl. These substituents may be further substituted.

The compounds of the general formulae (1) to (1''''), general formula (2), or general formula (2') having a substituted bipyridyl and triphenylene ring structure of the present invention are novel compounds. The compounds have faster electron mobility than conventional electron transport materials, and can maintain the stable thin-film state, making it possible to improve luminous efficiency, and lower driving voltage.

The bipyridyl bound to the triphenylene ring (when n1 to n5 are 2 in the general formula (1) or (2)) is preferably 2,2'-bipyridyl, 2,3'-bipyridyl, 2,4'-bipyzidyl, or 3,2'-bipyridyl, particularly preferably 2,2'-bipyridyl, or a 2,4'-bipyridyl.

The compounds of the general formulae (1) to (1''''), general formula (2), or general formula (2') having a substituted bipyridyl and triphenylene ring structure of the present invention can be used as the constituent material of the electron injection layer and/or the electron transport layer of an organic EL device. By using the material having higher electron injection and mobility than conventional materials, the efficiency of the electron transport from the electron transport layer to the light emitting layer improves. This improves the luminous efficiency, and lowers driving voltage, making it possible to improve the durability of the organic EL device.

The compounds of the general formulae (1) to (1''''), general formula (2), or general formula (2') having a substituted bipyridyl and triphenylene ring structure of the present invention also can be used as the constituent material of the light emitting layer of an organic EL device. When used as the host material of a light emitting layer to support the dopant phosphor or phosphorescent material for the use as a light emitting layer, the material of the present invention having a more desirable electron transport property and a wider band gap than conventional materials can provide an organic EL device of low driving voltage and improved luminous efficiency.

The organic EL device of the present invention can realize high efficiency and high durability, because it uses the compound having a substituted bipyridyl and triphenylene ring structure that has faster electron mobility and a more stable thin-film state than conventional electron transport materials.

Advantage of the Invention

The compounds having a substituted bipyridyl and triphenylene ring structure of the present invention have fast electron mobility and a stable thin-film state, and are useful as the constituent material of the electron injection layer, the electron transport layer, or the light emitting layer of an organic EL device. The organic EL device produced by using the compounds having a substituted bipyridyl and triphenylene ring structure can have improved luminous efficiency and low driving voltage, and can thus have improved durability.

MODE FOR CARRYING OUT THE INVENTION

Figure 1:
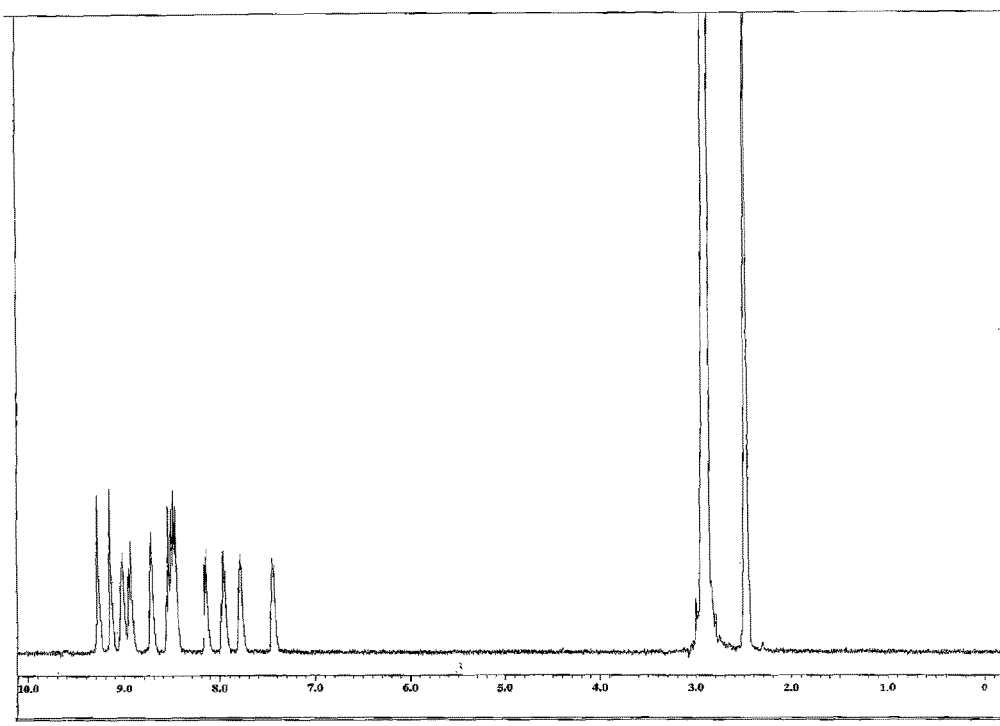
FIG. 1 is a $^1$H-NMR chart of the compound of Example 1 of the present invention (Compound 3).

The compounds having a substituted bipyridyl and triphenylene ring structure of the present invention are novel compounds, and may be synthesized by using, for example, the following method. First, the dihalide of a corresponding triphenylene compound is boronated with a compound such as bis(pinacolato)diboron to synthesize a corresponding borate product (refer to Non-Patent Document 5, for example), and this corresponding borate product is reacted with a halogenobipyridine having various substituents in a cross-coupling reaction such as Suzuki coupling (refer to Non-Patent Document 6, for example) to synthesize the compound having a substituted bipyridyl and triphenylene ring structure.

The compounds having a substituted bipyridyl and triphenylene ring structure also can be synthesized as follows. First, a halogenobipyridine having various substituents is boronated with a compound such as bis(pinacolato)diboron, and the resulting bipyridine borate product with various substituents is then reacted with the dihalide of a corresponding triphenylene compound in a cross-coupling reaction such as Suzuki coupling.

The following presents specific examples of preferred compounds among the compounds of general formulae (1) to (1''''), general formula (2), or general formula (2') having a substituted bipyridyl and triphenylene ring structure. The present invention, however, is not limited to these compounds.

[Chemical Formula 8]
(Compound 3)
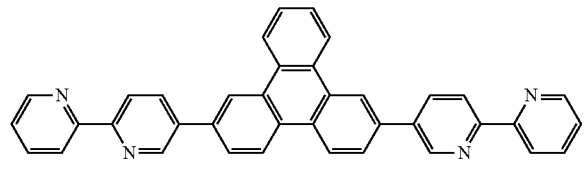
[Chemical Formula 9]
(Compound 4)
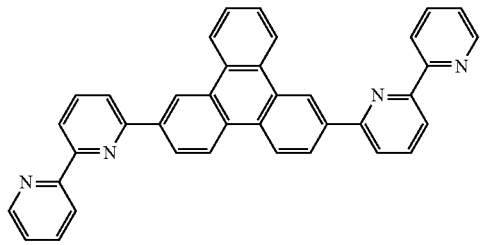
[Chemical Formula 10]
(Compound 5)
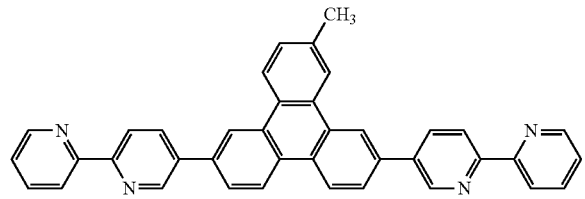
[Chemical Formula 11]
(Compound 6)
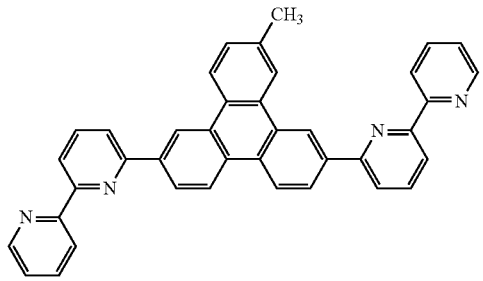
[Chemical Formula 12]
(Compound 7)
[Chemical Formula 13]
(Compound 8)
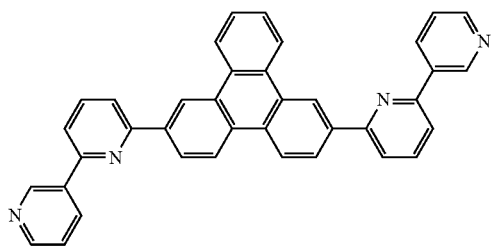
[Chemical Formula 14]
(Compound 9)
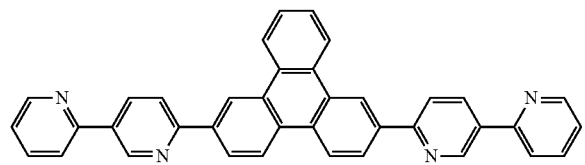
[Chemical Formula 15]
(Compound 10)
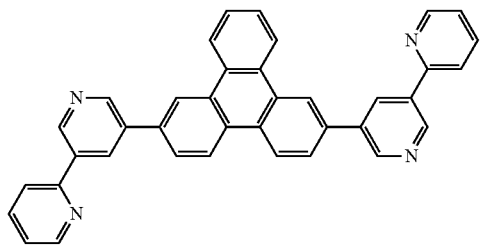

[Chemical Formula 16]
(Compound 11)
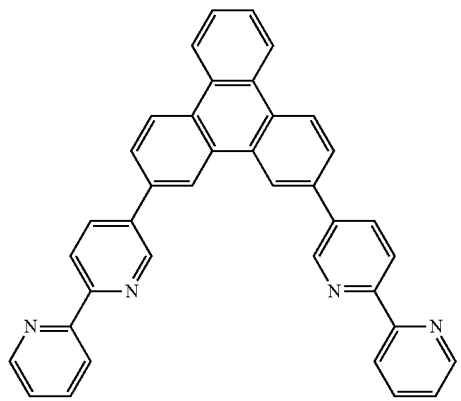
[Chemical Formula 17]
(Compound 12)
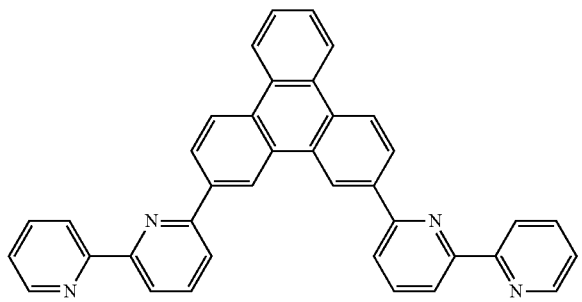
[Chemical Formula 18]
(Compound 13)
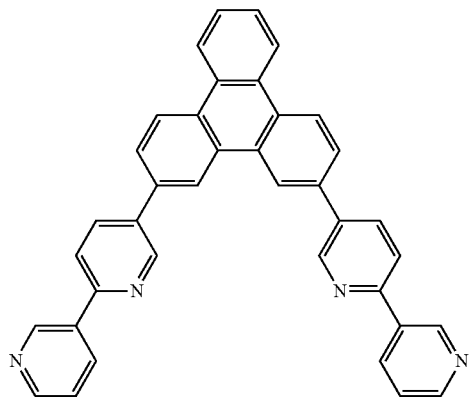
[Chemical Formula 19]
(Compound 14)
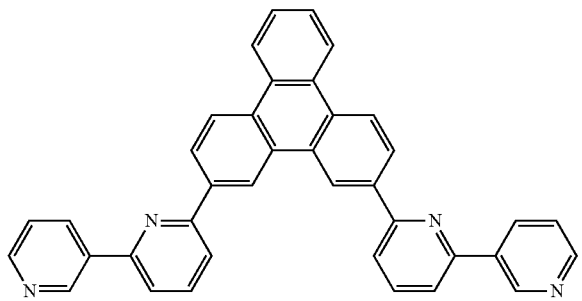
[Chemical Formula 20]
(Compound 15)
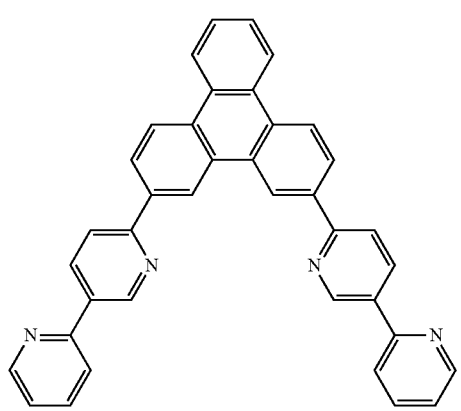
[Chemical Formula 21]
(Compound 16)
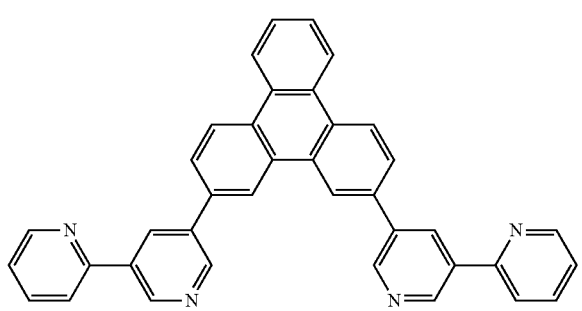

[Chemical Formula 22]
(Compound 17)
[Chemical Formula 23]
(Compound 18)
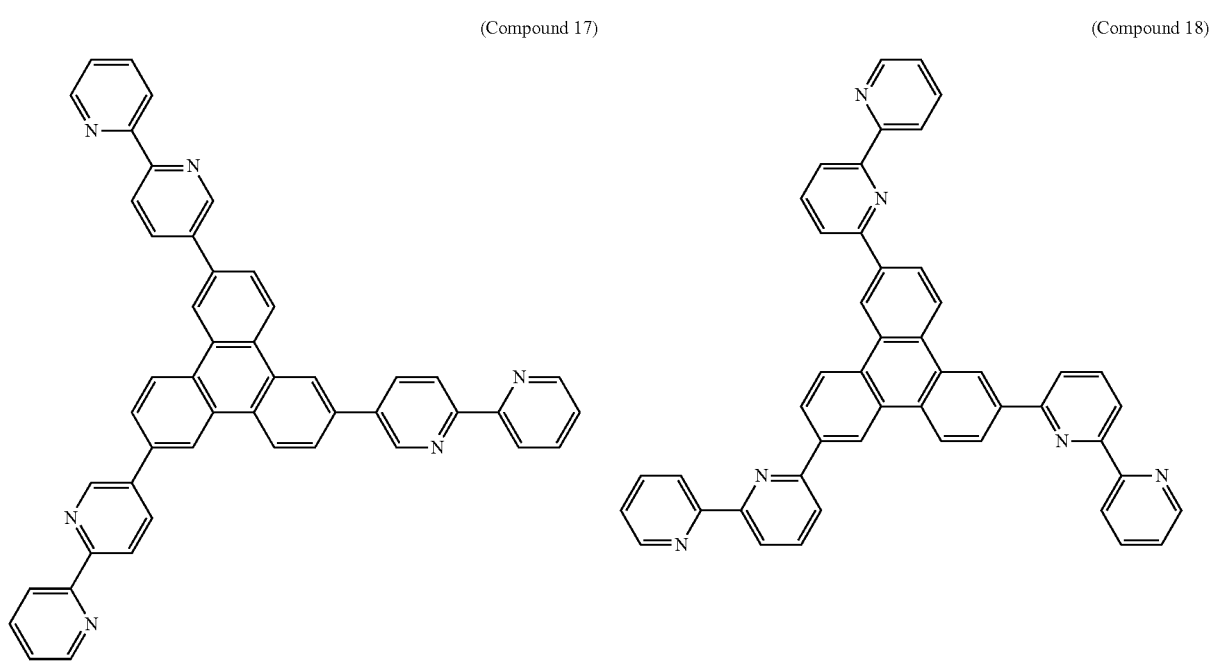
[Chemical Formula 24]
(Compound 19)
[Chemical Formula 25]
(Compound 20)
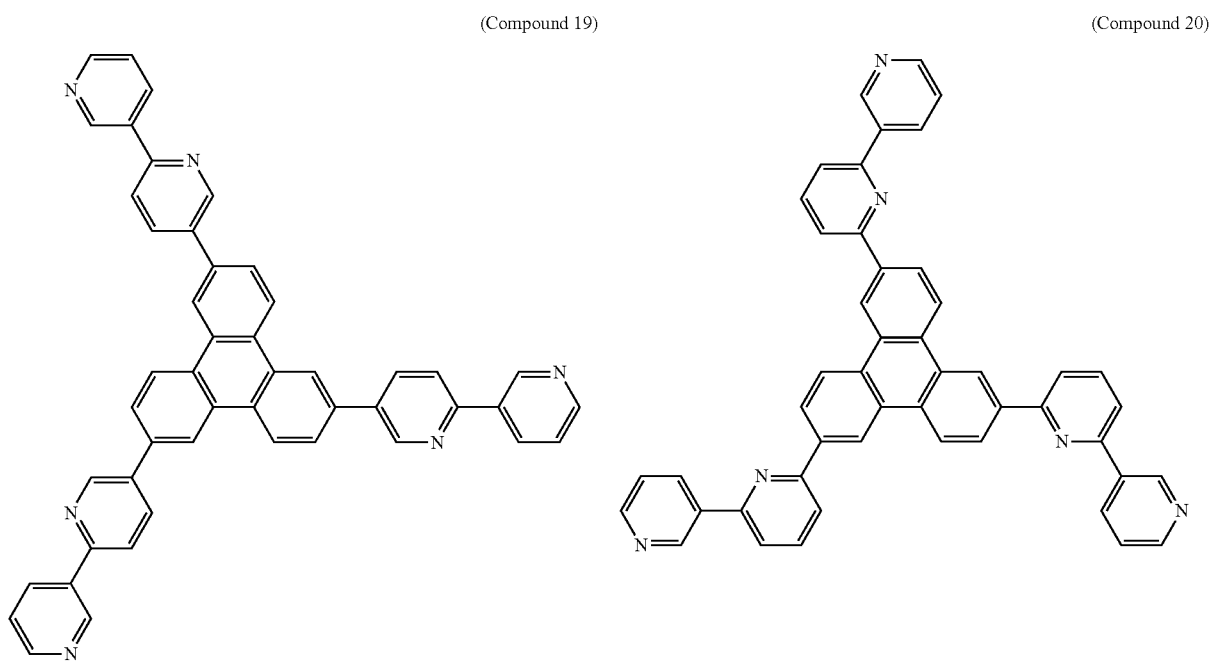

-continued
[Chemical Formula 26]
(Compound 21)
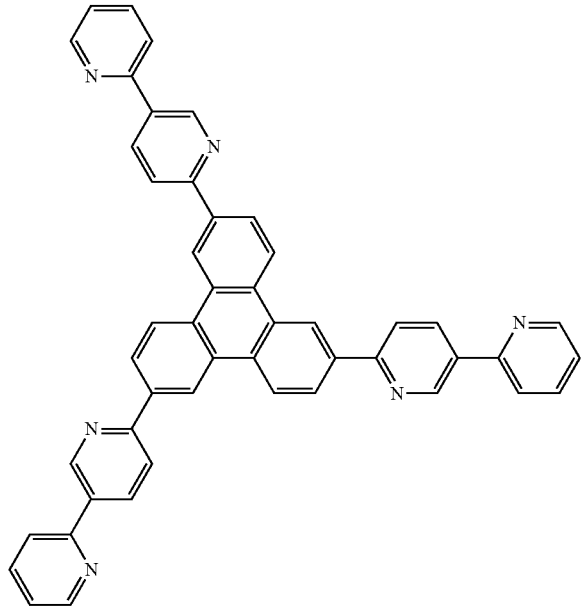
[Chemical Formula 27]
(Compound 22)
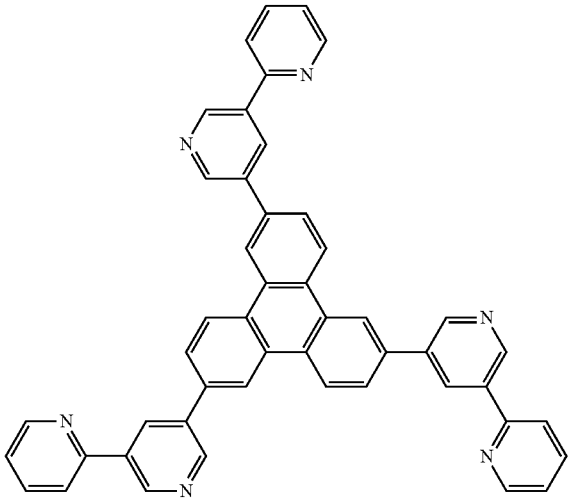
[Chemical Formula 28]
(Compound 23)
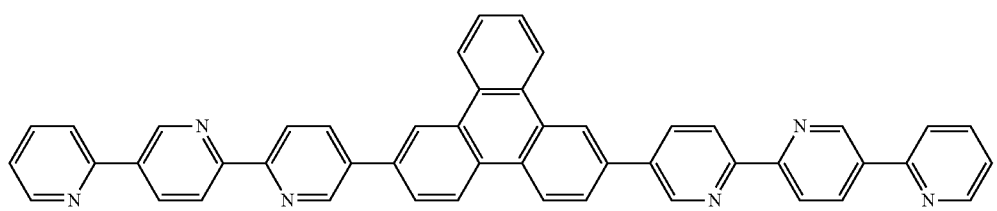
[Chemical Formula 29]
(Compound 24)
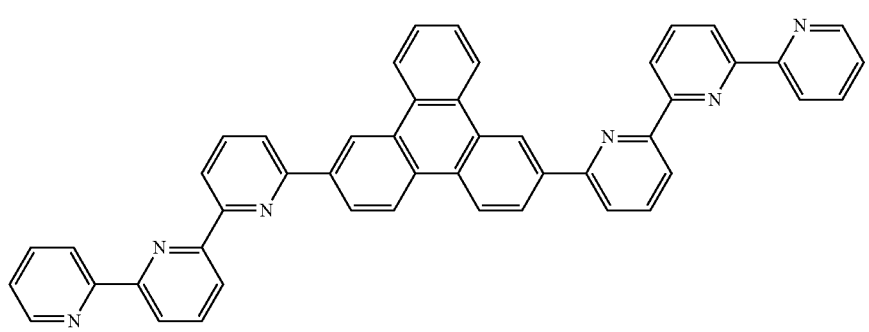
[Chemical Formula 30]
(Compound 25)
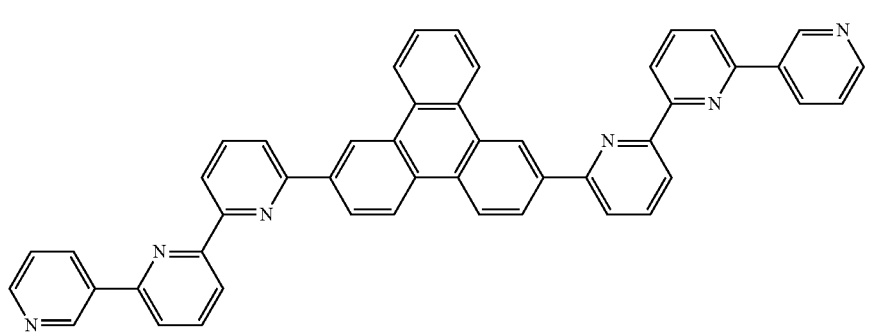

[Chemical Formula 31]
(Compound 26)
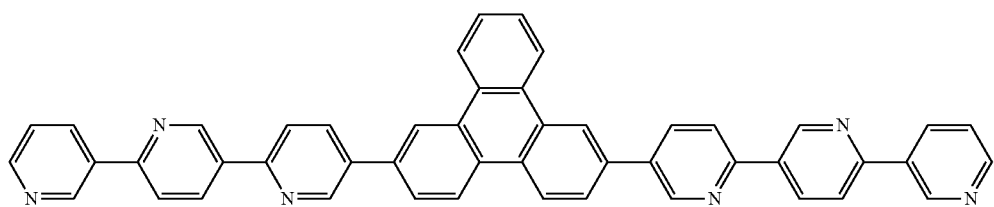
[Chemical Formula 32]
(Compound 27)
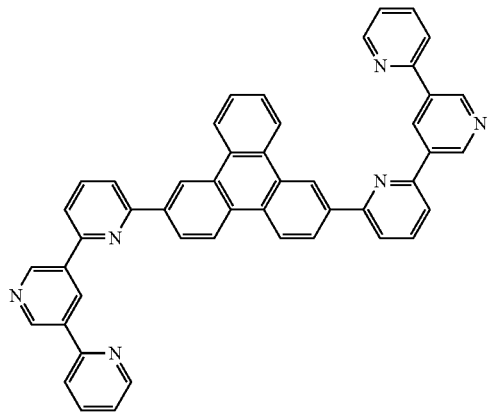
[Chemical Formula 33]
(Compound 28)
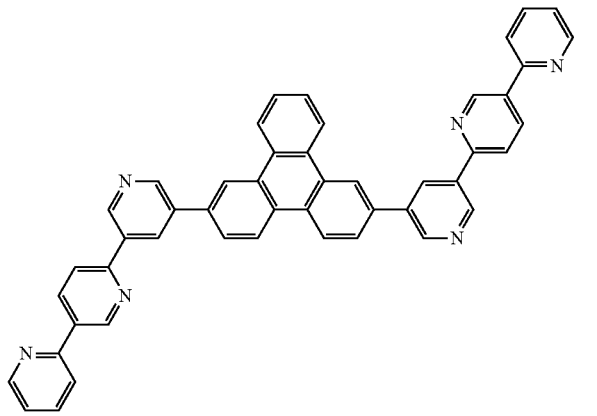
[Chemical Formula 34]
(Compound 29)
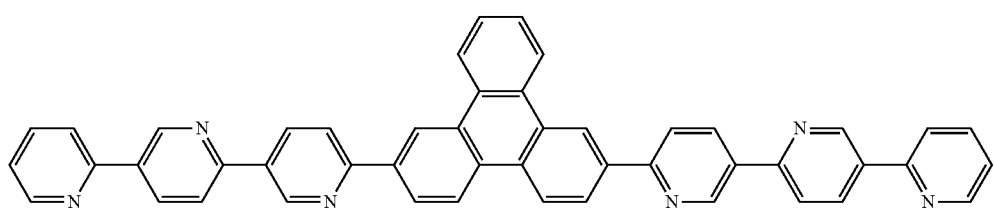
[Chemical Formula 35]
(Compound 30)
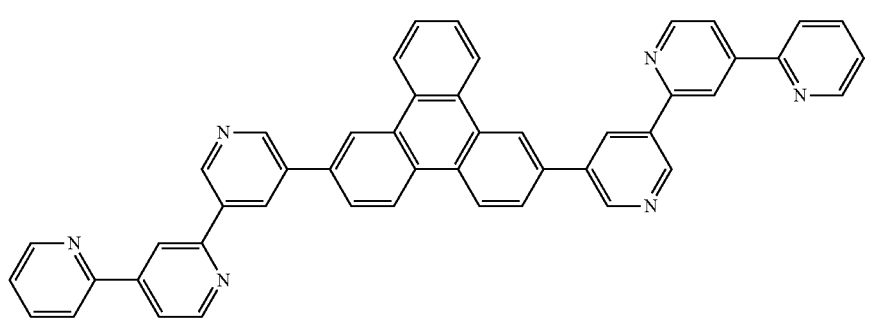

[Chemical Formula 36]
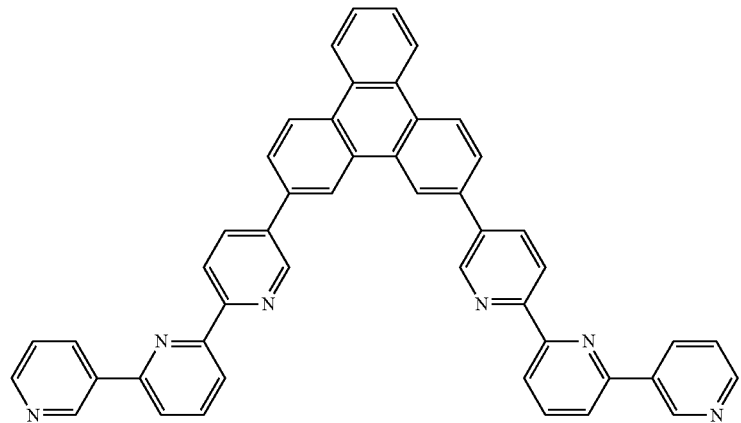
(Compound 31)
[Chemical Formula 37]
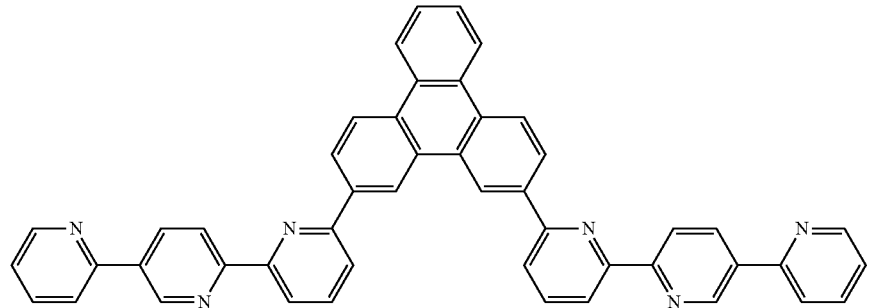
(Compound 32)
[Chemical Formula 38]                         [Chemical Formula 39]
(Compound 33)                         (Compound 34)
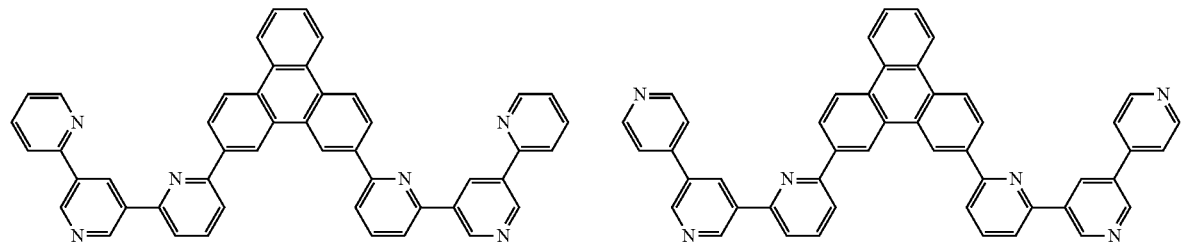

[Chemical Formula 40]
(Compound 35)
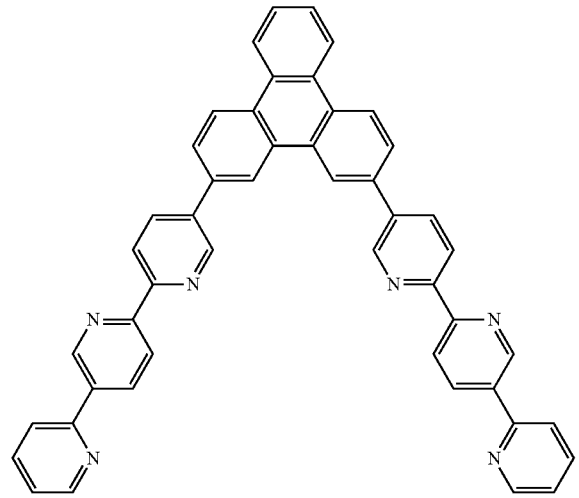
[Chemical Formula 41]
(Compound 36)
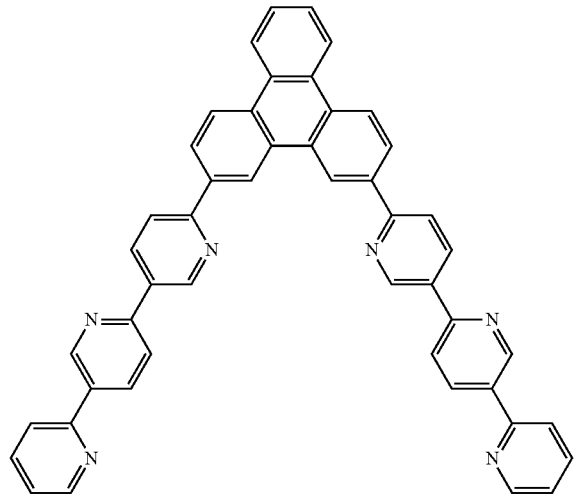
[Chemical Formula 42]
(Compound 37)
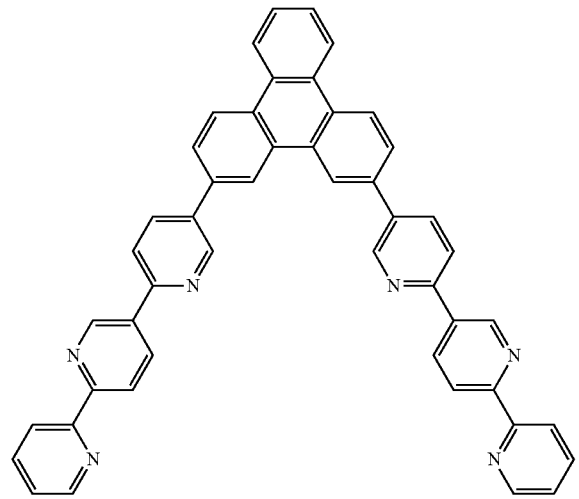
[Chemical Formula 43]
(Compound 38)
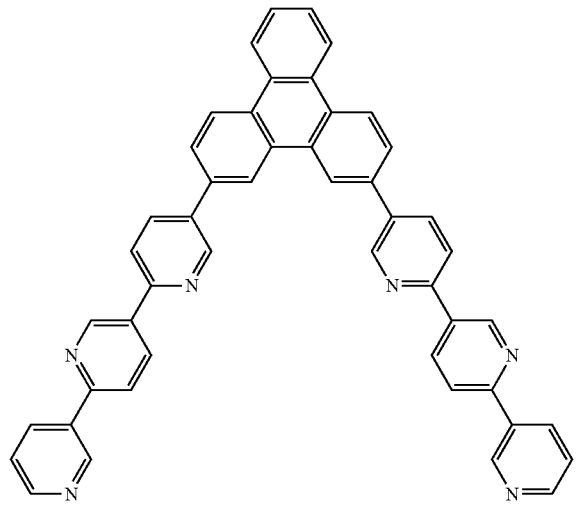

-continued
[Chemical Formula 44]
(Compound 39)
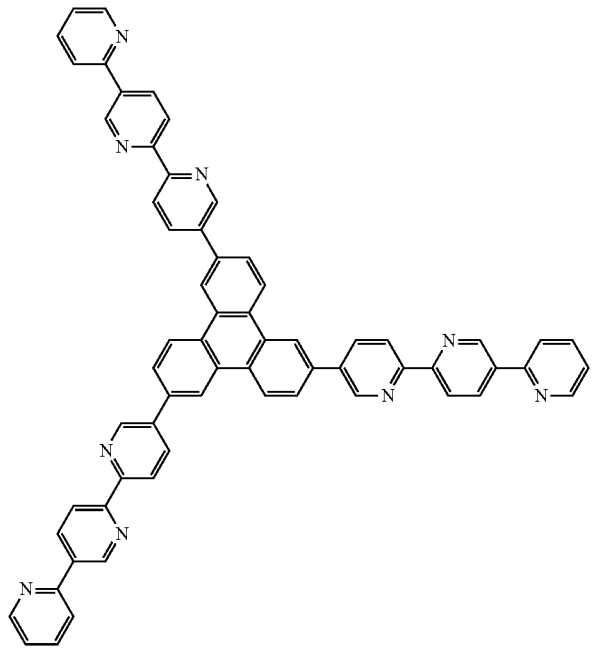
[Chemical Formula 45]
(Compound 40)
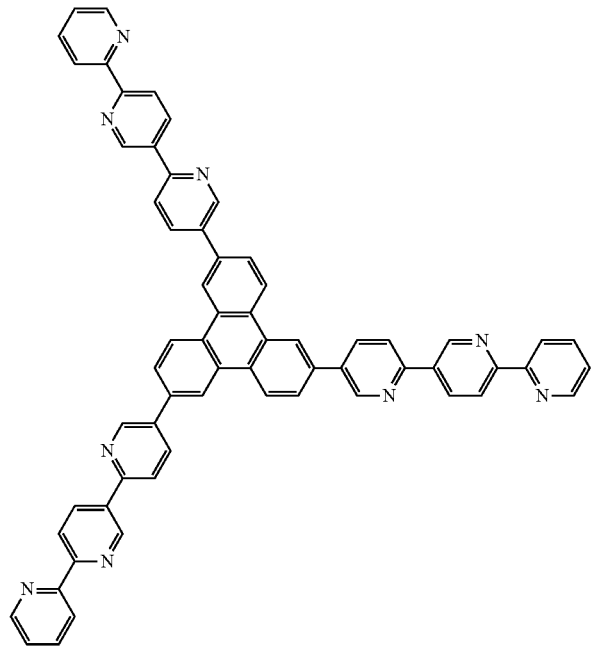
[Chemical Formula 46]
(Compound 41)
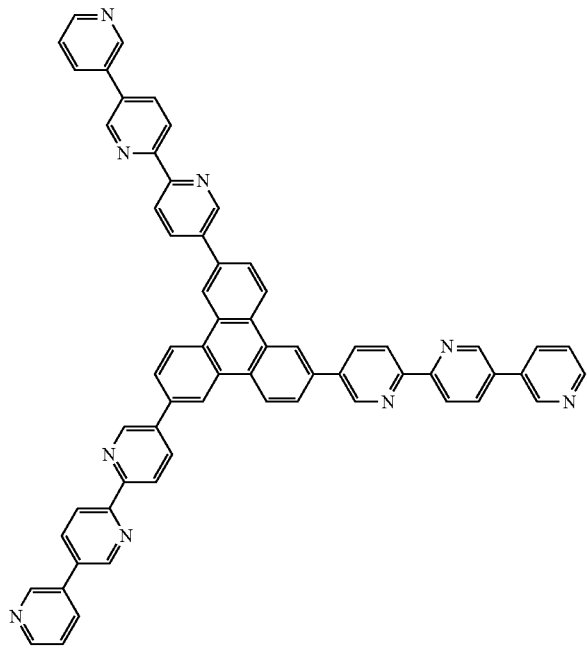
[Chemical Formula 47]
(Compound 42)
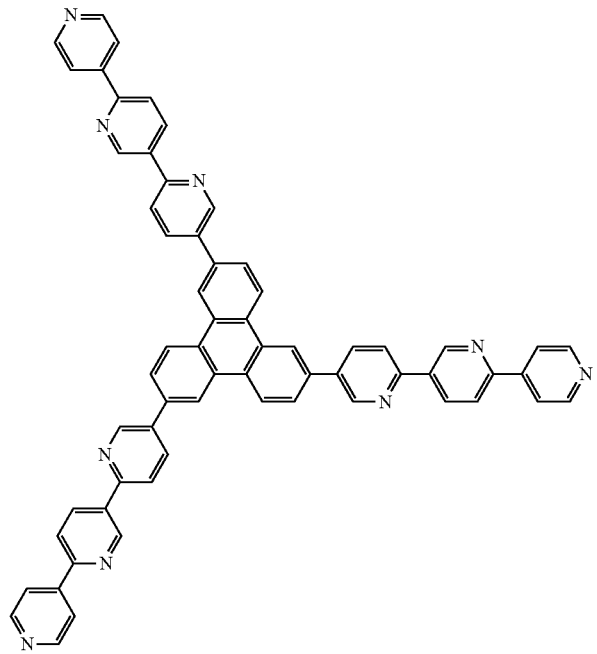

-continued
[Chemical Formula 48]
(Compound 43)
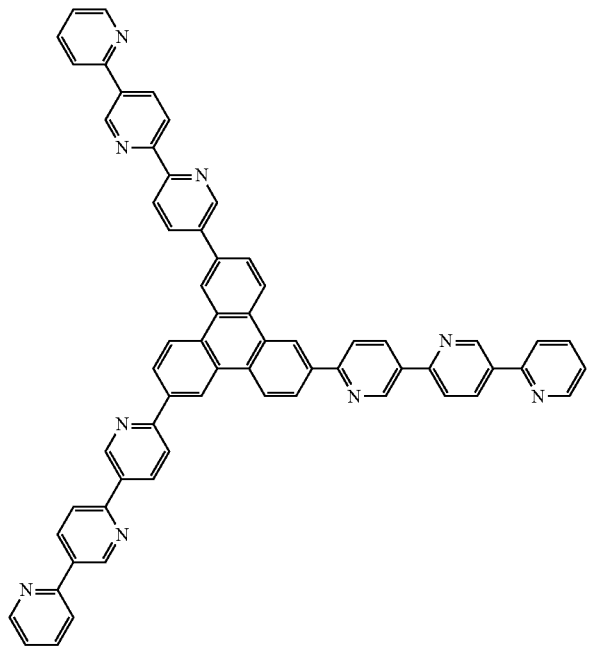
[Chemical Formula 49]
(Compound 44)
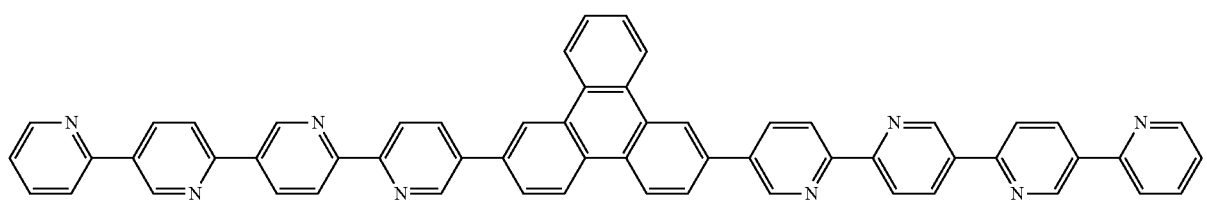
[Chemical Formula 50]
(Compound 45)
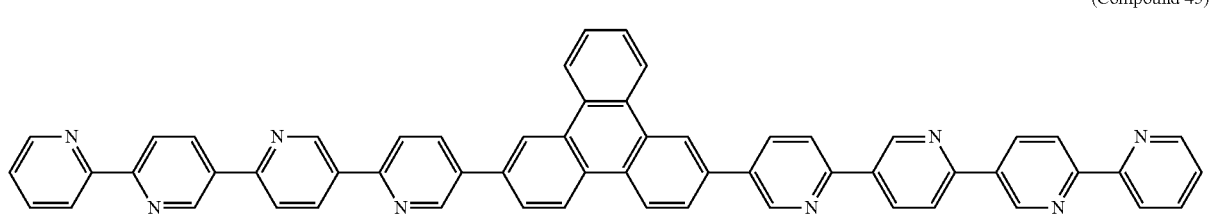
[Chemical Formula 51]
(Compound 46)
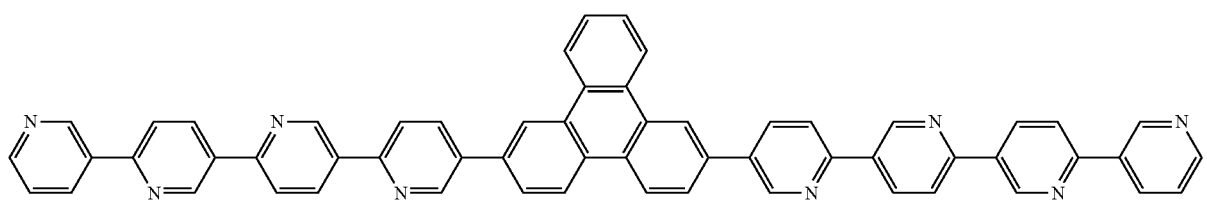

-continued
[Chemical Formula 52]
(Compound 47)
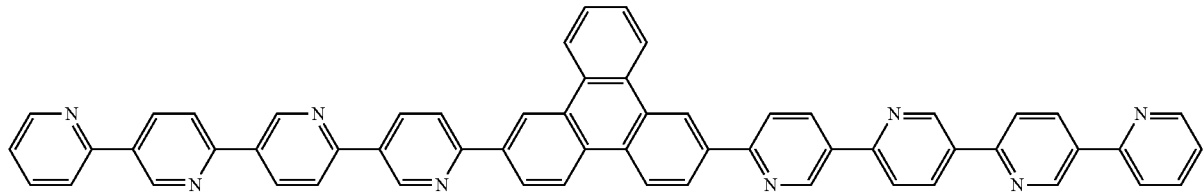
[Chemical Formula 53]
(Compound 48)
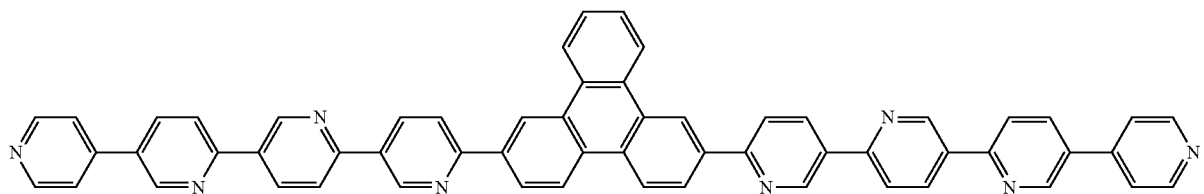
[Chemical Formula 54]     [Chemical Formula 55]
(Compound 49)     (Compound 50)
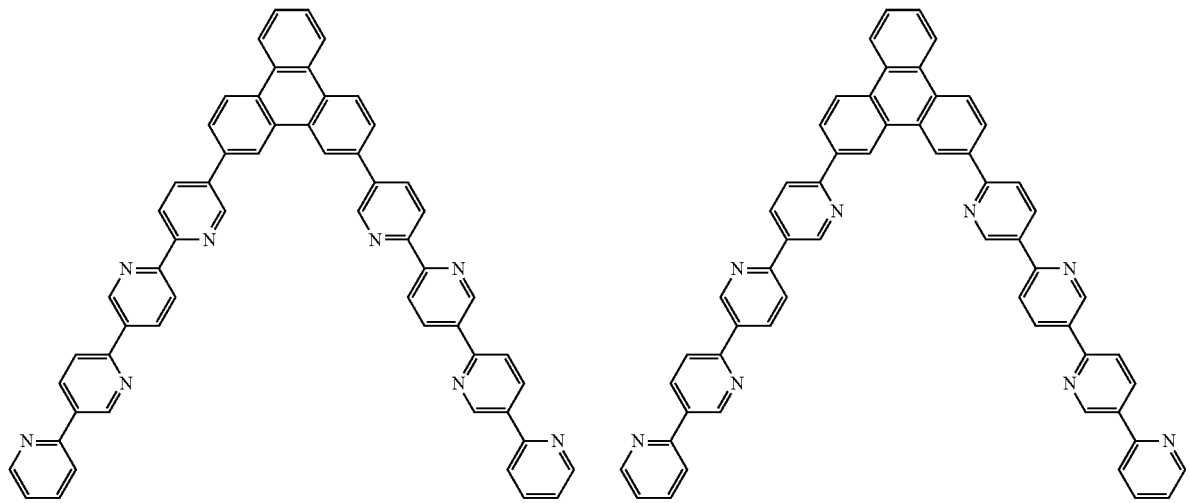
[Chemical Formula 56]     [Chemical Formula 57]
(Compound 51)     (Compound 52)
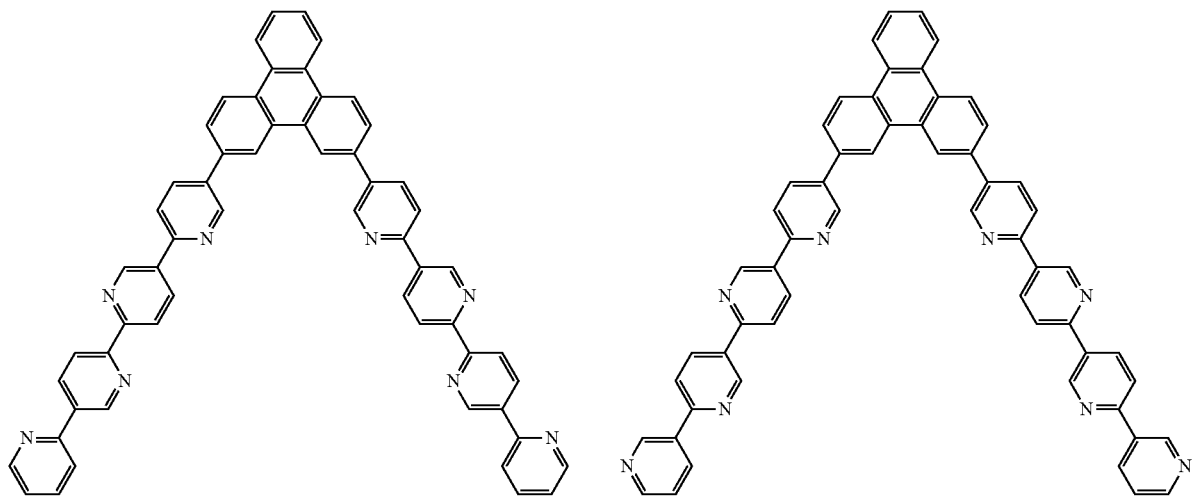

-continued

[Chemical Formula 58]

(Compound 53)

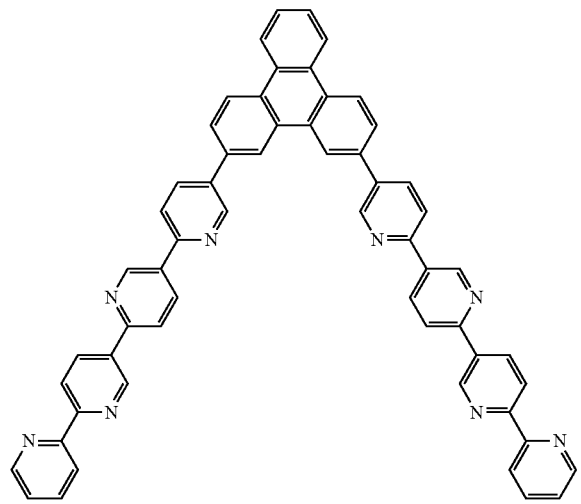

[Chemical Formula 59]

(Compound 54)

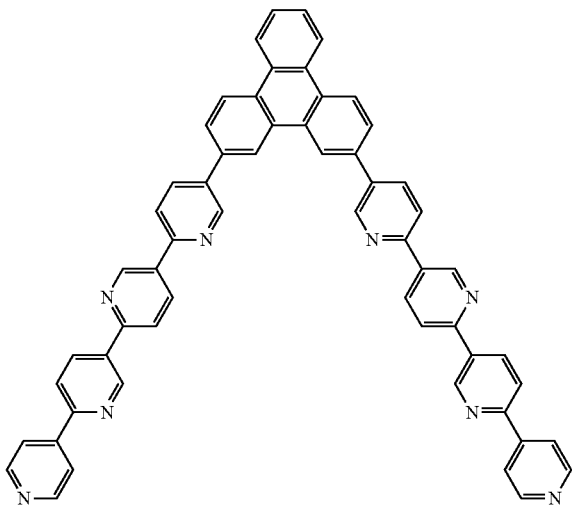

[Chemical Formula 60]

(Compound 55)

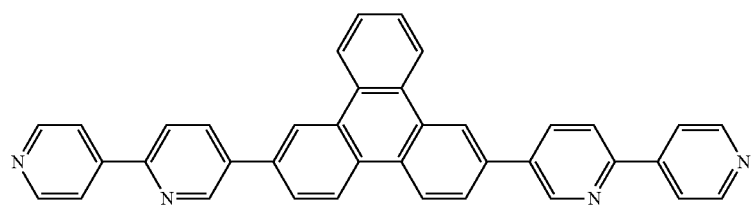

These compounds were purified by methods such as column chromatography, adsorption using, for example, a silica gel, activated carbon, or activated clay, and recrystallization or crystallization using a solvent. The compounds were identified by using methods such as NMR analysis, mass spectrometry, and elementary analysis. Melting point, glass transition point (Tg), and work function were taken for the measurement of physical properties. Melting point can be used as an index of ease of vapor deposition, glass transition point (Tg) as an index of stability in the thin-film state, and the work function as an index of hole blocking capability.

The melting point and the glass transition point (Tg) were measured using a powder, using a high-sensitive differential scanning calorimeter DSC3100S (Bruker AXS).

For the measurement of work function, a 100 nm-thick thin film was fabricated on an ITO substrate, and an atmosphere photoelectron spectrometer (AC-3; Riken Keiki Co., Ltd.) was used.

The organic EL device of the present invention may have a structure including an anode, a hole transport layer, a light emitting layer, a hole blocking layer, an electron transport layer, and a cathode successively formed on a substrate, optionally with a hole injection layer between the anode and the hole transport layer, an electron injection layer between the electron transport layer and the cathode, or an electron blocking layer between the light emitting layer and the hole transport layer. Some of the organic layers in this multilayer structure may be omitted. For example, the organic EL device may be configured to include an anode, a hole transport layer, a light emitting layer, an electron transport layer, and a cathode successively formed on a substrate.

Each of the light emitting layer, the hole transport layer, and the electron transport layer may have a laminate structure of two or more layers.

Electrode materials with a large work function, such as ITO and gold, are used as the anode of the organic EL device of the present invention. The hole injection layer of the organic EL device of the present invention may be made of various materials, including, for example, porphyrin compounds as represented by copper phthalocyanine, starburst-type triphenylamine derivatives, triphenylamine trimers and tetramers such as an arylamine compound of a structure in which three or more triphenylamine structures are joined to each other within the molecule via a single bond or a divalent group that does not contain a heteroatom, accepting heterocyclic compounds such as hexacyano azatriphenylene, and coating-type polymer materials. These materials may be formed into a thin film by using a vapor deposition method, or other known methods such as spin coating and an inkjet method.

Examples of the material used for the hole transport layer of the organic EL device of the present invention include benzidine derivatives [such as N,N'-diphenyl-N,N'-di(m-tolyl)-benzidine (hereinafter, referred to simply as "TPD"), N,N'-diphenyl-N,N'-di(α-naphthyl)-benzidine (hereinafter, referred to simply as "NPD"), and N,N,N',N'-tetrabiphenylylbenzidine], 1,1-bis[(di-4-tolylamino)phenyl]cyclohexane (hereinafter, referred to simply as "TAPC"), various triphenylamine trimers and tetramers, and carbazole derivatives. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. Examples of the material used for the hole injection/transport layer include coating-type polymer materials such as poly(3,4-ethylenedioxythiophene) (hereinafter, simply "PEDOT")/poly(styrene sulfonate) (hereinafter, simply "PSS"). These materials may be formed into a thin-film by using a vapor deposition method, or other known methods such as spin coating and an inkjet method.

Further, the hole injection layer or the hole transport layer may be one obtained by the P-doping of material such as trisbromophenylamine hexachloroantimony in the material commonly used for these layers. Further, for example, polymer compounds having a TPD structure as a part of the compound structure also may be used.

Examples of the material used for the electron blocking layer of the organic EL device of the present invention include compounds having an electron blocking effect, including, for example, carbazole derivatives such as 4,4',4"-tri(N-carbazolyl)triphenylamine (hereinafter, simply "TCTA"), 9,9-bis[4-(carbazol-9-yl)phenyl]fluorene, 1,3-bis(carbazol-9-yl)benzene (hereinafter, simply "mCP"), and 2,2-bis(4-carbazol-9-ylphenyl)adamantane (hereinafter, simply "Ad-Cz"); and compounds having a triphenylsilyl group and a triarylamine structure, as represented by 9-[4-(carbazol-9-yl)phenyl]-9-[4-(triphenylsilyl)phenyl]-9H-fluorene. These may be deposited alone, or may be used as a single layer deposited as a mixture with other materials, or as a laminate of individually deposited layers, a laminate of a layer deposited as a mixture, or a laminate of a layer deposited alone and a layer deposited as a mixture. These materials may be formed into a thin-film by using a vapor deposition method, or other known methods such as spin coating and an inkjet method.

Examples of the material used for the light emitting layer of the organic EL device of the present invention include quinolinol derivative metal complexes such as $Alq_3$, various metal complexes, anthracene derivatives, bis(styryl)benzene derivatives, pyrene derivatives, oxazole derivatives, and polyparaphenylene vinylene derivatives, in addition to the compounds having a substituted bipyridyl and triphenylene ring structure of the present invention. Further, the light emitting layer may be configured from a host material and a dopant material. Examples of the host material include thiazole derivatives, benzimidazole derivatives, and polydialkyl fluorene derivatives, in addition to the foregoing light-emitting materials. Examples of the dopant material include quinacridone, coumalin, rubrene, perylene, derivatives thereof, benzopyran derivatives, rhodamine derivatives, and aminostyryl derivatives. These may be deposited alone, or may be used as a single layer deposited as a mixture with other materials, or as a laminate of individually deposited layers, a laminate of layers deposited as a mixture, or a laminate of a layer deposited alone and a layer deposited as a mixture.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as $Ir(ppy)_3$, blue phosphorescent materials such as FIrpic and $FIr_6$, and red phosphorescent materials such as $Btp_2Ir(acac)$. Here, carbazole derivatives such as 4,4'-di(N-carbazolyl)biphenyl (hereinafter, simply "CBP"), TCTA, and mCP may be used as the hole injecting and transporting host material. Compounds such as p-bis(triphenylsilyl)benzene (hereinafter, simply "UGH2"), and 2,2',2"-(1,3,5-phenylene)-tris(1-phenyl-1H-benzimidazole) (hereinafter, simply "TPBI") may be used as the electron transporting host material.

In order to avoid concentration quenching, the doping of the phosphorescent light-emitting material in the host material should preferably be made by co-evaporation in a range of 1 to 30 weight percent with respect to the whole light emitting layer.

These materials may be formed into a thin-film by using a vapor deposition method, or other known methods such as spin coating and an inkjet method.

The hole blocking layer of the organic EL device of the present invention may be formed by using hole blocking compounds such as various rare earth complexes, oxazole derivatives, triazole derivatives, and triazine derivatives, in addition to the compounds having a substituted bipyridyl and triphenylene ring structure of present invention, and metal complexes of phenanthroline derivatives such as bathocuproin (hereinafter, simply "BCP"), and metal complexes of quinolinol derivatives such as BAlq. These materials may also serve as the material of the electron transport layer. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin-film by using a vapor deposition method, or other known methods such as spin coating and an inkjet method.

Examples of the material used for the electron transport layer of the organic EL device of the present invention include various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to the compounds having a substituted bipyridyl and triphenylene ring structure of the present invention, and quinolinol derivative metal complexes such as $Alq_3$ and BAlq. These may be deposited alone, or may be used as a single layer deposited as a mixture with other materials, or as a laminate of individually deposited layers, a laminate of layers deposited as a mixture, or a laminate of a layer deposited alone and a layer deposited as a mixture. These materials may be formed into a thin-film by using a vapor deposition method, or other known methods such as spin coating and an inkjet method.

Examples of the material used for the electron injection layer of the organic EL device of the present invention include alkali metal salts (such as lithium fluoride, and cesium fluoride), alkaline earth metal salts (such as magnesium fluoride), and metal oxides (such as aluminum oxide), in addition to the compounds having a substituted bipyridyl and triphenylene ring structure of the present invention. However, the electron injection layer may be omitted upon preferably selecting the electron transport layer and the cathode.

The electron injection layer or the electron transport layer may be one obtained by the N-doping of metals such as cesium in the materials commonly used for these layers.

The cathode of the organic EL device of the present invention may be made of an electrode material having a low work function (such as aluminum), or an alloy of an electrode material having an even lower work function (such as a magnesium-silver alloy, a magnesium-indium alloy, or an aluminum-magnesium alloy).

The following describes an embodiment of the present invention in more detail based on Examples. The present invention, however, is not limited to the following Examples.

Example 1

<Synthesis of 2,7-bis(2,2'-bipyridin-5-yl)triphenylene (Compound 3)>

2,5-Dibromopyridine (19.5 g), 2-pyridylzinc bromide (150 ml), tetrahydrofuran (90 ml), and tetrakis(triphenylphosphine)palladium(0) (4.33 g) were added to a nitrogen-substituted reaction vessel. After being cooled, the mixture was stirred at 0° C. for 2 hours, and then at room temperature for 3 hours. The reaction mixture was added to a 10% disodium dihydrogen ethylenediamine tetraacetate aqueous solution, and stirred for 6 hours. The organic layer was collected by separation after adding chloroform (300 ml). The organic layer was dried over anhydrous magnesium sulfate, and concentrated to obtain a crude product. The crude product was purified by column chromatography (support: silica gel, eluent: toluene) to obtain a white powder of 5-bromo-2,2'-bipyridine (11.1 g; yield 63%).

Separately, 1,2-diiodobenzene (24.4 g), 3-trimethylsilylphenylboronic acid (30 g), sodium hydroxide (8.8 g), tetrakis(triphenylphosphine)paladium(0) (4.3 g), diethylene glycol dimethyl ether (160 ml), and water (40 ml) were added to a nitrogen-substituted reaction vessel. The mixture was heated, and stirred at 95° C. for 15 hours. After cooling the mixture to room temperature, water (100 ml) was added, and the organic layer was collected by separation. The organic layer was washed two times with water (100 ml), dried over anhydrous magnesium sulfate, and concentrated to obtain a crude product. The crude product was purified by column chromatography (support: silica gel, eluent: n-hexane) to obtain a white powder of 3,3"-bis(trimethylsilyl)-1,1':2',1"-terphenyl (23.3 g; yield 84%).

The 3,3"-bis(trimethylsilyl)-1,1':2',1"-terphenyl (23 g), bromine (12.6 ml), and chloroform (1.80 ml) were added to a nitrogen-substituted reaction vessel. The mixture was cooled, and stirred at −5° C. for 3 hours, and then at room temperature for 4 hours. The organic layer was collected by separation after adding a saturated sodium sulfite aqueous solution (90 ml). The organic layer was then washed two times with water (100 ml), dried over anhydrous magnesium sulfate, and concentrated to obtain a crude product. The crude product was purified by recrystallization with ethanol, and washed with methanol to obtain a white powder of 3,3"-dibromo-1,1':2',1"-terphenyl (15.4 g; yield 65%).

The 3,3"-dibromo-1,1':2',1"-terphenyl (12.0 g), molybdenum chloride(V) (16.9 g), and dichloromethane (20 ml) were added to a nitrogen-substituted reaction vessel, and stirred at room temperature for 19 hours. After adding water (100 ml), the reaction mixture was stirred for 30 minutes, and the precipitate was collected by filtration, and washed with methanol to obtain a crude product. After adding chloroform (200 ml), n-hexane (600 ml), and silica gel (36.6 g), the crude product was purified by adsorption, and washed with chloroform to obtain a pale yellow powder of 2,7-dibromotriphenylene (5.5 g; yield 46%).

The 2,7-dibromotriphenylene (5.5 g), bis(pinacolato)diboron (7.9 g), potassium acetate (4.2 g), 1,4-dioxane (50 ml) predried with a 4A molecular sieve, and a [1,1'-bis(diphenylphosphino)ferrocene]palladium(II)dichloride-dichloromethane complex (1:1; 0.4 g) were added to a nitrogen-substituted reaction vessel. The mixture was heated, and stirred at 80° C. for 10 hours. Chloroform (150 ml) was added after cooling the mixture to 50° C., and the mixture was stirred for 30 minutes. The insoluble matter was removed by filtration, and the filtrate was concentrated to obtain a crude product. The crude product was purified by column chromatography [support: silica gel, eluent: ethyl acetate/n-hexane=1/5 (v/v)] to obtain a white powder of 2,7-bis(4,4,5,5-tetramethyl-[1,3,2]dioxaboroan-2-yl)triphenylene (4.8 g; yield 70%).

The 2,7-bis(4,4,5,5-tetramethyl-[1,3,2]dioxaboroan-2-yl)triphenylene (2.4 g), the 5-bromo-2,2'-bipyridine (2.5 g), a 2 M potassium carbonate aqueous solution (7.7 ml), tetrakis(triphenylphosphine)palladium(0) (0.3 g), toluene (40 ml), and ethanol (10 ml) were added to a nitrogen-substituted reaction vessel. The mixture was heated, and refluxed for 9 hours while being stirred. After cooling the mixture to room temperature, the precipitate was collected by filtration. The precipitate was dissolved in chloroform (2,000 ml), and purified by adsorption with a silica gel (11.5 g). The product was recrystallized from 1,2-dichlorobenzene to obtain a yellow powder of 2,7-bis(2,2'-bipyridin-5-yl)triphenylene (compound 3; 1.6 g; yield 60%).

The structure of the product yellow powder was identified by NMR. The $^1$H-NMR measurement result is shown in FIG. 1.

$^1$H-NMR (DMSO-$d_6$) detected 24 hydrogen signals, as follows. δ (ppm)=9.28 (2H), 9.15 (2H), 9.02-9.03 (2H), 8.93-8.96 (2H), 8.72 (2H), 8.47-8.56 (6H), 8.14-8.16 (2H), 7.94-7.98 (2H), 7.78-7.79 (2H), 7.43-7.46 (2H).

Example 2

<Synthesis of 2,7-bis(2,2'-bipyridin-6-yl)triphenylene (Compound 4)>

2,6-Dibromopyridine (19.5 g), 2-pyridylzinc bromide (150 ml), tetrahydrofuran (90 ml), and tetrakis(triphenylphosphine)palladium(0) (4.33 g) were added to a nitrogen-substituted reaction vessel. The mixture was cooled, and stirred at 0° C. for 2 hours, and then at room temperature for 3 hours. The reaction mixture was added to a 10% disodium dihydrogen ethylenediamine tetraacetate aqueous solution, and stirred for 6 hours. The organic layer was collected by separation after adding chloroform (300 ml). The organic layer was dried over anhydrous magnesium sulfate, and concentrated to obtain a crude product. The crude product was purified by column chromatography (support: silica gel, eluent: toluene) to obtain a white powder of 6-bromo-2,2'-bipyridine (11.1 g; yield 63%).

The 6-bromo-2,2'-bipyridine (2.4 g), the 2,7-bis(4,4,5,5-tetramethyl-[1,3,2]dioxaboroan-2-yl)triphenylene (2.3 g) synthesized in Example 1, a 2 M potassium carbonate aqueous solution (7.4 ml), tetrakis(triphenylphosphine)palladium(0) (0.3 g), toluene (40 ml), and ethanol (10 ml) were added to a nitrogen-substituted reaction vessel. The mixture was heated, and refluxed for 9 hours while being stirred. After cooling the mixture to room temperature, the precipitate was collected by filtration. The insoluble matter was removed by filtration with chloroform (1,300 ml), and the product was purified by recrystallization with 1,2-dichlorobenzene to obtain a pale yellowish white powder of 2,7-bis(2,2'-bipyridin-6-yl)triphenylene (compound 4; 1.7 g; yield 66%).

Figure 2:
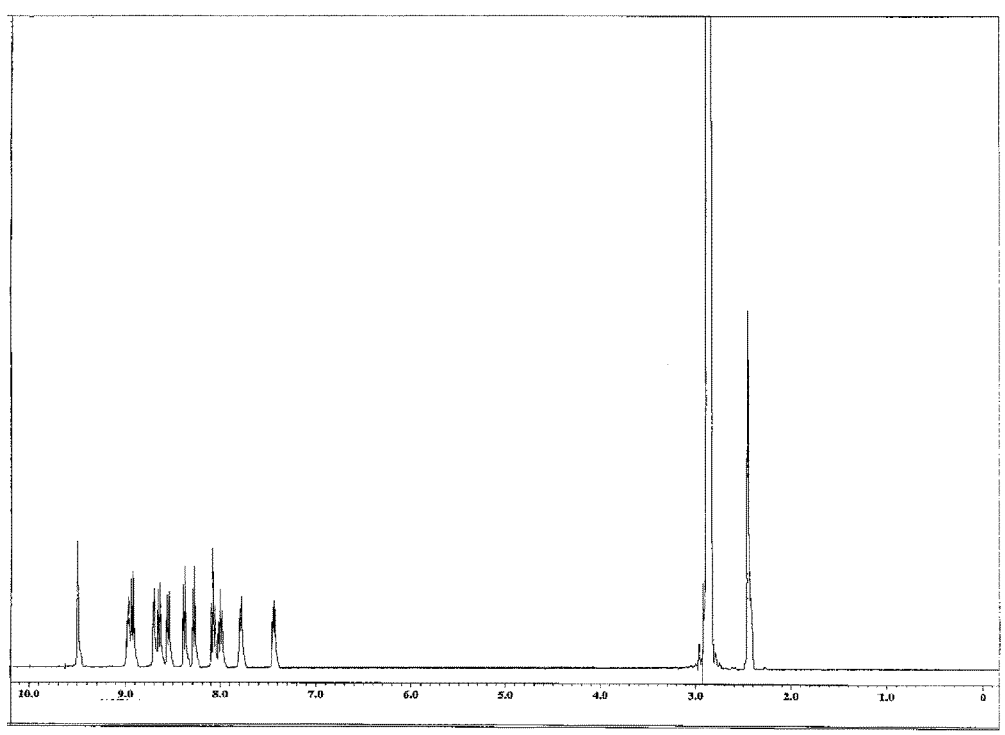
FIG. 2 is a $^1$H-NMR chart of the compound of Example 2 of the present invention (Compound 4).

The structure of the product pale yellowish white powder was identified by NMR. The $^1$H-NMR measurement result is shown in FIG. 2.

$^1$H-NMR (DMSO-$d_6$) detected 24 hydrogen signals, as follows. δ (ppm)=9.50 (2H), 8.92-8.98 (4H), 8.64-8.70 (4H), 8.54-8.57 (2H), 8.38-8.40 (2H), 8.28-8.30 (2H), 8.06-8.10 (2H), 7.98-8.01 (2H), 7.78-7.80 (2H), 7.43-7.45 (2H).

Example 3

<Synthesis of 2,11-bis(2,2'-bipyridin-5-yl)triphenylene (Compound 11)>

1,2-Dibromobenzene (10 g), bis(pinacolato)diboron (23.7 g), potassium acetate (12.5 g), 1,4-dioxane (150 ml) predried with a 4A molecular sieve, and a [1,1'-bis(diphenylphosphino)ferrocene]palladium(II)dichloride-dichloromethane complex (1:1; 1.0 g) were added to a nitrogen-substituted reaction vessel. The mixture was heated, and stirred at 80° C. for 10 hours. Chloroform (150 ml) was added after cooling the mixture to 50° C., and the mixture was stirred for 30 minutes. The insoluble matter was removed by filtration, and the filtrate was concentrated to obtain a crude product. The crude product was purified by column chromatography [support: silica gel, eluent: ethyl acetate/n-hexane=1/4 (v/v)] to obtain a white powder of 1,2-bis(4,4,5,5-tetramethyl-[1,3,2]dioxabororan-2-yl)benzene (7.2 g; yield 54%).

Separately, 3,3'-dimethoxy-1,1'-biphenyl (30 g), bromine (15.8 ml), and acetic acid (250 ml) were added to a nitrogen-substituted reaction vessel, and the mixture was stirred at room temperature for 2 hours. After adding a saturated sodium sulfite aqueous solution (90 ml) to the reaction mixture, the organic layer was collected by separation with chloroform (200 ml). The organic layer was washed two times with water (100 ml), dried over anhydrous magnesium sulfate, and concentrated to obtain a crude product. The crude product was washed with ethanol to obtain a white powder of 2,2'-dibromo-3,3'-dimethoxy-1,1'-biphenyl (36.3 g; yield 70%).

The 2,2'-dibromo-3,3'-dimethoxy-1,1'-biphenyl (2.8 g), the 1,2-bis(4,4,5,5-tetramethyl-[1,3,2]dioxabororan-2-yl)benzene (3.0 g), potassium phosphate (9.6 g), tetrakis(triphenylphosphine)palladium(0) (0.43 g), tetrahydrofuran (50 ml), and water (15 ml) were added to a nitrogen-substituted reaction vessel. The mixture was heated, and stirred at 60° C. for 48 hours. After cooling the mixture to room temperature, the organic layer was collected by separation after adding chloroform (100 ml). The organic layer was washed two times with water (50 ml), dried over anhydrous magnesium sulfate, and concentrated to obtain a crude product. The crude product was purified by column chromatography [support: silica gel, eluent: ethyl acetate/n-hexane/methylene chloride=1/10/1 (v/v/v)], and washed with methanol to obtain a white powder of 2,11-dimethoxytriphenylene (1.72 g; 65.6%).

The 2,11-dimethoxytriphenylene (1.5 g), a boron tribromide:dichloromethane solution (1 mol/L; 10.9 ml), and dichloromethane (50 ml) were added to a nitrogen-substituted reaction vessel cooled to −78° C. The mixture was heated to room temperature, and stirred for 20 hours. After adding water (50 ml) to the reaction mixture, the mixture was stirred for 30 minutes, and the precipitate was collected by filtration. The precipitate was washed with methanol to obtain a white powder of triphenylene-2,11-diol (1.25 g; yield 93%).

The triphenylene-2,11-diol (1.25 g), N-phenyl-bis(trifluoromethanesulfoneimide) (6.87 g), sodium carbonate (5.1 g), and dimethylformamide (50 ml) were added to a nitrogen-substituted reaction vessel, and the mixture was stirred at room temperature for 12 hours. After adding water (50 ml) to the reaction mixture, the mixture was stirred for 30 minutes, and the precipitate was collected by filtration. The precipitate was washed with methanol to obtain a white powder of triphenylene-2,11-diyl-bis(trifluoromethanesulfonate) (2.38 g; yield 91%).

The triphenylene-2,11-diyl-bis(trifluoromethanesulfonate) (2.3 g), bis(pinacolato)diboron (2.5 g), potassium acetate (1.3 g), 1,4-dioxane (50 ml) predried with a 4A molecular sieve, and a [1,1'-bis(diphenylphosphino)ferrocene]palladium(II)dichloride-dichloromethane complex (1:1; 0.1 g) were added to a nitrogen-substituted reaction vessel. The mixture was heated, and stirred at 80° C. for 10 hours. Chloroform (150 ml) was added after cooling the mixture to 50° C., and the mixture was stirred for 30 minutes. The insoluble matter was removed by filtration, and the filtrate was concentrated to obtain a crude product. The crude product was purified by column chromatography [support: silica gel, eluent: ethyl acetate/n-hexane=1/5 (v/v)] to obtain a white powder of 2,11-bis(4,4,5,5-tetramethyl-[1,3,2]dioxabororan-2-yl)triphenylene (1.1 g; yield 52%).

The 2,11-bis(4,4,5,5-tetramethyl-[1,3,2]dioxabororan-2-yl)triphenylene (0.9 g), the 5-bromo-2,2'-bipyridine (0.9 g) synthesized in Example 1, a 2 M potassium carbonate aqueous solution (2.9 ml), tetrakis(triphenylphosphine)palladium(0) (0.1 g), toluene (40 ml), and ethanol (10 ml) were added to a nitrogen-substituted reaction vessel. The mixture was heated, and refluxed for 9 hours while being stirred. After cooling the mixture to room temperature, the precipitate was collected by filtration. The precipitate was dissolved in chloroform (1,000 ml), and purified by adsorption with a silica gel (11.5 g). The product was then recrystallized from 1,2-dichlorobenzene to obtain a yellow powder of 2,11-bis(2,2'-bipyridin-5-yl)triphenylene (compound 11; 0.7 g; yield 70%).

Figure 3:
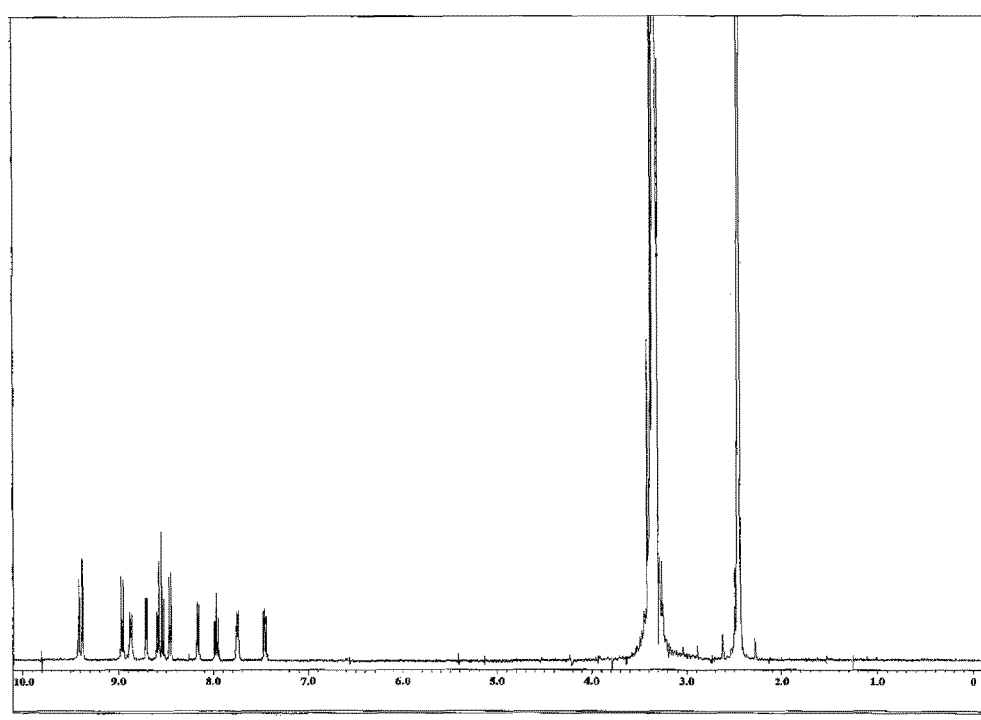
FIG. 3 is a $^1$H-NMR chart of the compound of Example 3 of the present invention (Compound 11).

The structure of the product yellow powder was identified by NMR. The $^1$H-NMR measurement result is shown in FIG. 3.

$^1$H-NMR (DMSO-$d_6$) detected 24 hydrogen signals, as follows. δ (ppm)=9.41 (2H), 9.37 (2H), 9.95 (2H), 8.88-8.85 (2H), 8.71 (2H), 8.60-8.57 (2H), 8.56-8.54 (2H), 8.52-8.45 (2H), 8.16 (2H), 7.95-7.98 (2H), 7.74 (2H), 7.45 (2H).

Example 4

<Synthesis of 2,11-bis(2,2'-bipyridin-6-yl)triphenylene (Compound 12)>

The 2,11-bis(4,4,5,5-tetramethyl-[1,3,2]dioxabororan-2-yl)triphenylene (0.8 g) synthesized in Example 3, the 6-bromo-2,2'-bipyridine (0.8 g) synthesized in Example 2, a 2 M potassium carbonate aqueous solution (2.3 ml), tetrakis(triphenylphosphine)palladium(0) (0.1 g), toluene (40 ml), and ethanol (10 ml) were added to a nitrogen-substituted reaction vessel. The mixture was heated, and refluxed for 9 hours while being stirred. After cooling the mixture to room temperature, the precipitate was collected by filtration. Chloroform (1,300 ml) was added to the precipitate, and the insoluble matter was removed by filtration. The product was then purified by recrystallization with 1,2-dichlorobenzene to obtain a pale yellowish white powder of 2,11-bis(2,2'-bipyridin-6-yl)triphenylene (compound 12; 0.6 g; yield 71%).

Figure 4:
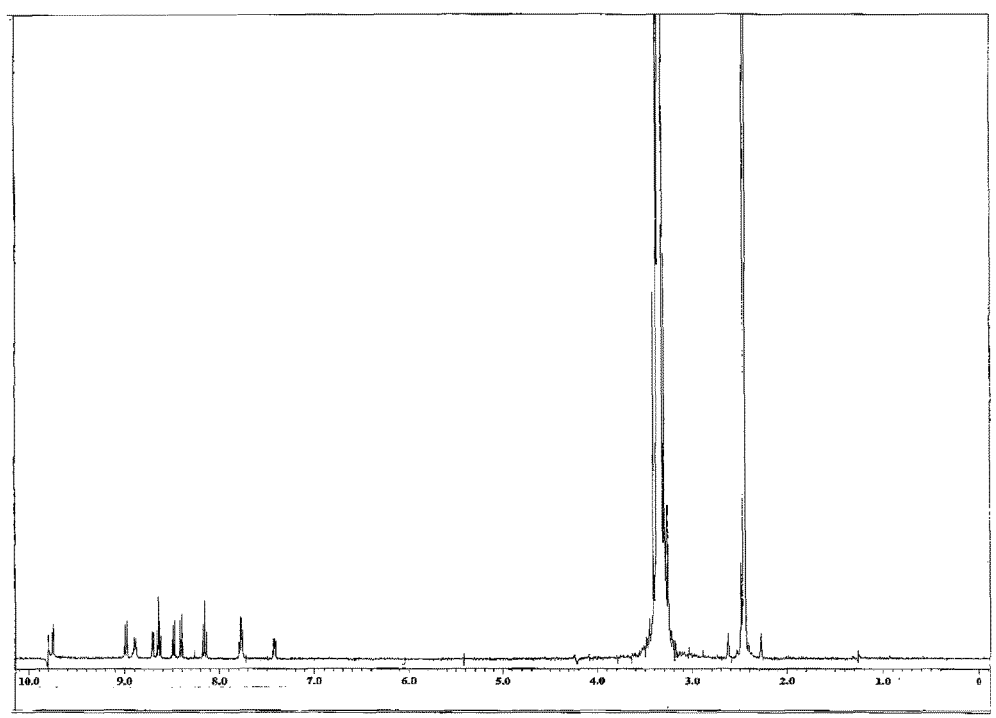
FIG. 4 is a $^1$H-NMR chart of the compound of Example 4 of the present invention (Compound 12).

The structure of the product pale yellowish white powder was identified by NMR. The $^1$H-NMR measurement result is shown in FIG. 4.

$^1$H-NMR (DMSO-$d_6$) detected 24 hydrogen signals, as follows. δ (ppm)=9.74 (2H), 8.98 (2H), 8.90-8.87 (2H), 8.70

(2H), 8.66-8.62 (4H), 8.48 (2H), 8.41 (2H), 8.17-8.13 (2H), 7.79-7.75 (4H), 7.43-7.40 (2H).

Example 5

<Synthesis of 2,7-di([2,4'-bipyridin]-5-yl)triphenylene (Compound 55)>

2,5-Dibromopyridine (9.6 g), 4-pyridineboronic acid (2.5 g), toluene (50 ml), ethanol (40 ml), a 2 M potassium carbonate aqueous solution (15.2 ml), and tetrakis(triphenylphosphine)palladium(0) (1.50 g) were added to a nitrogen-substituted reaction vessel. The mixture was heated, and refluxed for 24 hours while being stirred. After cooling the mixture to room temperature, chloroform (500 ml) and water (300 ml) were added, and the organic layer was collected by separation. The organic layer was washed two times with water (100 ml), dried over anhydrous magnesium sulfate, and concentrated to obtain a crude product. The crude product was purified by column chromatography [support: silica gel, eluent: toluene:ethyl acetate=1:1 (v/v)] to obtain a white powder of 5-bromo-2,4'-bipyridine (3.3 g; yield 69%).

The 5-bromo-2,4'-bipyridine (2.4 g), the 2,7-bis(4,4,5,5-tetramethyl-[1,3,2]dioxabororan-2-yl)triphenylene (2.0 g) synthesized in Example 1, a 2 M potassium carbonate aqueous solution (6.3 ml), tetrakis(triphenylphosphine)palladium(0) (0.3 g), toluene (40 ml), and ethanol (25 ml) were added to a nitrogen-substituted reaction vessel. The mixture was heated, and refluxed for 24 hours while being stirred. After cooling the mixture to room temperature, the precipitate was collected by filtration. Chloroform (1,300 ml) was added to the precipitate, and the insoluble matter was removed by filtration. The product was then purified by recrystallization with 1,2-dichlorobenzene to obtain a pale yellowish white powder of 2,7-di([2,4'-bipyridin]-5-yl)triphenylene (compound 55; 1.1 g; yield 50%).

The structure of the pale yellowish white powder was identified by using a matrix-assisted laser desorption/ionization time-of-flight mass spectrometer (AXIMA-CFR Plus; Shimadzu Corporation), and an elementary analysis device (Yanaco CHNCORDER MT-5; Yanamoto Seisakusho).

MS (m/z) 537 [calculated value (m/z) 536.20], elementary analysis, measured value: C; 85.08, H; 4.42, N; 10.39, calculated value ($C_{38}H_{24}N_4$): C; 85.05, H; 4.51, N; 10.44.

Comparative Synthesis Example 1

<Synthesis of 3,3"-bis(2,2'-bipyridin-5-yl)-1,1':2',1"-terphenyl (Comparative Compound 1)>

The 3,3"-dibromo-1,1':2',1"-terphenyl (5.0 g) synthesized in Example 1, bis(pinacolato)diboron (6.9 g), potassium acetate (3.8 g), 1,4-dioxane (50 ml) predried with a 4A molecular sieve, and a [1,1'-bis(diphenylphosphino)ferrocene]palladium(II)dichloride-dichloromethane complex (1:1; 0.3 g) were added to a nitrogen-substituted reaction vessel. The mixture was heated, and stirred at 80° C. for 11 hours. Chloroform (100 ml) was added after cooling the mixture to 50° C., and the mixture was stirred for 30 minutes. The insoluble matter was removed by filtration, and the filtrate was concentrated to obtain a crude product. The crude product was purified by column chromatography [support: silica gel, eluent: ethyl acetate/n-hexane=1/20 (v/v) to obtain a white powder of 3,3'-bis(4,4,5,5-tetramethyl-[1,3,2]dioxabororan-2-yl)-1,1':2',1'-terphenyl (3.8 g; yield 61%).

The 3,3"-bis(4,4,5,5-tetramethyl-[1,3,2]dioxabororan-2-yl)-1, 1':2',1'"-terphenyl (1.8 g), the 5-bromo-2,2'-bipyridine (1.8 g) synthesized in Example 1, a 2 M potassium carbonate aqueous solution (5.8 ml), tetrakis(triphenylphosphine)palladium(0) (0.2 g), toluene (40 ml), and ethanol (10 ml) were added to a nitrogen-substituted reaction vessel. The mixture was heated, and refluxed for 20 hours while being stirred. After cooling the mixture to room temperature, water (30 ml) and chloroform (100 ml) were added, and the organic layer was collected by separation. The organic layer was washed with water (100 ml), dried over anhydrous magnesium sulfate, and concentrated to obtain a crude product. The crude product was purified by column chromatography [support: NH silica gel, eluent: ethyl acetate/n-hexane=1/5 (v/v)] to obtain a white powder of 3,3"-bis(2,2'-bipyridin-5-yl)-1,1':2',1"-terphenyl represented by the following structural formula (comparative compound 1; 1.5 g; yield 80%).

[Chemical Formula 61]

(comparative compound 1)

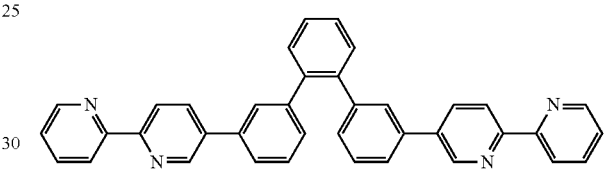

The structure of the product white powder was identified by NMR.

$^1$H-NMR (CDCl$_3$) detected 26 hydrogen signals, as follows. δ (ppm)=8.65-8.66 (2H), 8.51-8.53 (2H), 8.31-8.33 (2H), 8.08 (2H), 7.99-8.01 (2H), 7.71-7.79 (4H), 7.59-7.61 (2H), 7.54-7.56 (2H), 7.50-7.52 (2H), 7.34-7.38 (2H), 7.25-7.28 (4H).

Comparative Synthesis Example 2

<Synthesis of 3,3"-bis(2,2'-bipyridin-6-yl)-1,1':2',1"-terphenyl (Comparative Compound 2)>

The 3,3"-bis(4,4,5,5-tetramethyl-[1,3,2]dioxabororan-2-yl)-1, 1':2',1"-terphenyl (1.8 g) synthesized in Comparative Synthesis Example 1, the 6-bromo-2,2'-bipyridine (1.8 g) synthesized in Example 2, a 2 M potassium carbonate aqueous solution (5.8 ml), tetrakis(triphenylphosphine)palladium(0) (0.2 g), toluene (40 ml), and ethanol (10 ml) were added to a nitrogen-substituted reaction vessel. The mixture was heated, and refluxed for 8 hours while being stirred. After cooling the mixture to room temperature, water (30 ml) and toluene (40 ml) were added, and the organic layer was collected by separation. The organic layer was washed with water (30 ml), dried over anhydrous magnesium sulfate, and concentrated to obtain a crude product. The crude product was purified by column chromatography [support: NH silica gel, eluent: ethyl acetate/n-hexane=1/5 (v/v)] to obtain a white powder of 3,3"-bis(2,2'-bipyridin-6-yl)-1,1': 2',1"-terphenyl represented by the following structural formula (comparative compound 2; 1.5 g; yield 75%).

[Chemical Formula 62]

(comparative compound 2)

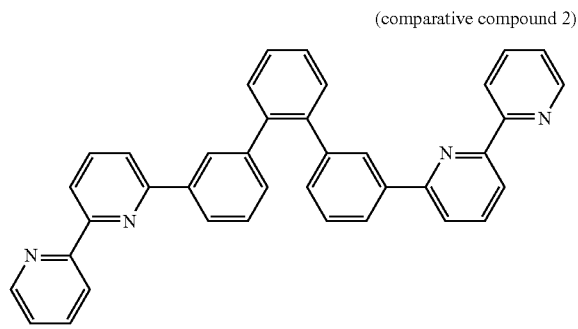

The structure of the product white powder was identified by NMR.

$^1$H-NMR (CDCl$_3$) detected 26 hydrogen signals, as follows. δ (ppm)=8.66-8.68 (4H), 8.35-8.40 (4H), 7.79-7.83 (2H), 7.69-7.72 (2H), 7.45-7.58 (8H), 7.35-7.39 (4H), 7.28-7.31 (2H).

Comparative Synthesis Example 3

<Synthesis of 4,4"-bis(2,2'-bipyridin-6-yl)-1,1':2',1"-terphenyl (Comparative Compound 3)>

1,2-Diiodobenzene (20 g), 4-trimethylsilylphenylboronic acid (25 g), sodium hydroxide (7.4 g), tetrakis(triphenylphosphine)palladium(0) (3.6 g), diethylene glycol dimethyl ether (240 ml), and water (60 ml) were added to a nitrogen-substituted reaction vessel. The mixture was heated, and stirred at 95° C. for 15 hours. Water (100 ml) was added after cooling the mixture to room temperature, and the organic layer was collected by separation. The organic layer was washed two times with water (100 ml), dried over anhydrous magnesium sulfate, and concentrated to obtain a crude product. The crude product was purified by column chromatography (support: silica gel, eluent: n-hexane) to obtain a white powder of 4,4"-bis(trimethylsilyl)-1,1':2',1"-terphenyl (21.1 g; yield 93%).

The 4,4"-bis(trimethylsilyl)-1,1':2',1"-terphenyl (21 g), bromine (11.5 ml), and chloroform (150 ml) were added to a nitrogen-substituted reaction vessel. The mixture was cooled, and stirred at −5° C. for 3 hours, and then at room temperature for 4 hours. The organic layer was collected by separation after adding a saturated sodium sulfite aqueous solution (90 ml). The organic layer was then washed two times with water (100 ml), dried over anhydrous magnesium sulfate, and concentrated to obtain a crude product. The crude product was purified by recrystallization with ethanol, and washed with methanol to obtain a white powder of 4,4"-dibromo-1,1':2',1"-terphenyl (14.9 g; yield 68%).

The 4,4"-dibromo-1,1':2',1"-terphenyl (5.0 g), bis(pinacolato)diboron (7.2 g), potassium acetate (3.8 g), 1,4-dioxane (50 ml) predried with a 4A molecular sieve, and a [1,1'-bis(diphenylphosphino)ferrocene]palladium(II)dichloride-dichloromethane complex (1:1; 0.3 g) were added to a nitrogen-substituted reaction vessel. The mixture was heated, and stirred at 80° C. for 10 hours. Chloroform (150 ml) was added after cooling the mixture to 50° C., and the mixture was stirred for 30 minutes. The insoluble matter was removed by filtration, and the filtrate was concentrated to obtain a crude product. The crude product was purified by column chromatography [support: silica gel, eluent: ethyl acetate/n-hexane=1/5 (v/v)] to obtain a white powder of 4,4"-bis(4,4,5,5-tetramethyl-[1,3,2]dioxabororan-2-yl)-1,1':2',1"-terphenyl (3.5 g; yield 56%).

The 4,4"-bis(4,4,5,5-tetramethyl-[1,3,2]dioxabororan-2-yl)-1, 1':2',1"-terphenyl (2.0 g), the 6-bromo-2,2'-bipyridine (2.0 g) synthesized in Example 2, a 2 M potassium carbonate aqueous solution (6.0 ml), tetrakis(triphenylphosphine)palladium(0) (0.2 g), toluene (32 ml), and ethanol (8 ml) were added to a nitrogen-substituted reaction vessel. The mixture was heated, and refluxed for 9 hours while being stirred. Water (100 ml) was added after cooling the mixture to room temperature, and the organic layer was collected by separation. The organic layer was washed two times with water (100 ml), dried over anhydrous magnesium sulfate, and concentrated to obtain a crude product. The crude product was purified by column chromatography (support: silica gel, eluent: chloroform), and recrystallized with toluene to obtain a white powder of 4,4"-bis(2,2'-bipyridin-6-yl)-1,1': 2',1"-terphenyl represented by the following structural formula (comparative compound 3; 1.6 g; yield 74%).

[Chemical Formula 63]

(comparative compound 3)

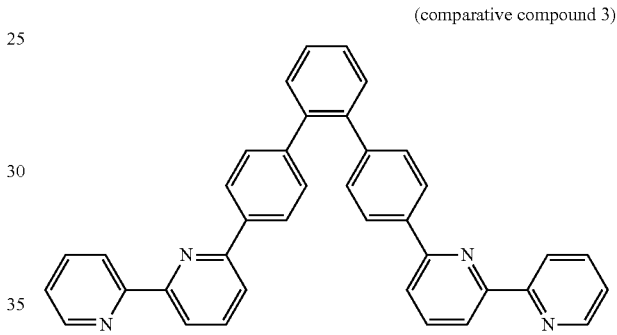

The structure of the product white powder was identified by NMR.

$^1$H-NMR (CDCl$_3$) detected 26 hydrogen signals, as follows. δ (ppm)=8.67 (2H), 8.60 (2H), 8.33 (2H), 8.06 (4H), 7.78-7.86 (4H), 7.74 (2H), 7.53-7.48 (4H), 7.36 (4H), 7.30-7.28 (2H).

Example 6

The melting points and the glass transition points of the compounds of the present invention were determined using a high-sensitive differential scanning calorimeter (DSC 3100S; Bruker AXS).

|  | Melting point | Glass transition point |
| --- | --- | --- |
| Compound of Example 1 of the present invention | 338° C. | None |
| Compound of Example 2 of the present invention | 285° C. | None |

The compounds of the present invention were not shown to have glass transition points. This indicates that the compounds of the present invention have a stable thin-film state.

Example 7

A 50 nm-thick vapor-deposited film was fabricated on an ITO substrate using the compounds of the present invention.

The work function was measured using an atmosphere photoelectron spectrometer (Model AC-3 produced by Riken Keiki Co., Ltd.).

|  | Work function |
|---|---|
| Compound of Example 1 of the present invention | 5.74 eV |
| Compound of Example 2 of the present invention | 5.69 eV |
| Compound of Example 3 of the present invention | 5.82 eV |
| Compound of Example 4 of the present invention | 5.73 eV |
| Compound of Example 5 of the present invention | 6.21 eV |

As shown above, the compounds of the present invention have work functions greater than the work function 5.4 eV of common hole transport materials such as NPD and TPD, and have high hole blocking capability.

Example 8

Figure 5:
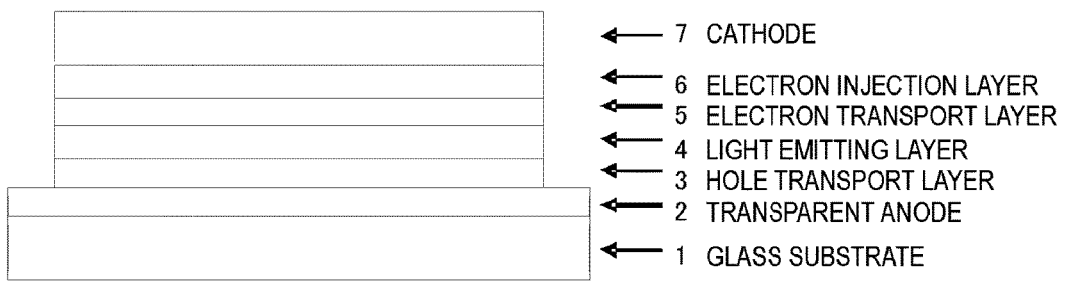
FIG. 5 is a diagram representing the configuration of the EL devices of Examples 8 to 11 and Comparative Examples 1 to 5.

The organic EL device, as illustrated in FIG. 5, was fabricated from a hole transport layer 3, a light emitting layer 4, an electron transport layer 5, an electron injection layer 6, and a cathode (silver electrode) 7 successively formed by vapor deposition on a glass substrate 1 that had been provided beforehand with an ITO electrode as a transparent anode 2.

Specifically, the glass substrate 1 having ITO (thickness 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less. This was followed by formation of the hole transport layer 3 by vapor depositing NPD over the transparent anode 2 in a thickness of 50 nm at a deposition rate of 2 Å/s. The light emitting layer 4 was then formed on the hole transport layer 3 by forming $Alq_3$ in a thickness of 20 nm at a deposition rate of 2 Å/s. Then, the electron transport layer 5 was formed on the light emitting layer 4 by forming the compound of Example 1 of the present invention (compound 3) in a thickness of 30 nm at a deposition rate of 2 Å/s. The electron injection layer 6 was then formed on the electron transport layer 5 by forming a magnesium silver alloy in a thickness of 100 nm at a deposition rate of 3.3 Å/s. Finally, the cathode 7 was formed by vapor depositing silver in a thickness of 10 nm. The characteristics of the organic EL device thus fabricated were measured in an atmosphere at ordinary temperature.

Table 1 summarizes the results of the emission characteristics measurements performed by applying a DC voltage to the organic EL device fabricated with the compound of Example 1 of the present invention (compound 3).

Example 9

An organic EL device was fabricated under the same conditions used in Example 8, except that the material of the electron transport layer 5 used in Example 8 was changed to the compound of Example 3 of the present invention (compound 11). The characteristics of the organic EL device thus fabricated were measured in an atmosphere at ordinary temperature. Table 1 summarizes the results of the emission characteristics measurements performed by applying a DC voltage to the organic EL device.

Example 10

An organic EL device was fabricated under the same conditions used in Example 8, except that the material of the electron transport layer 5 used in Example 8 was changed to the compound of Example 5 of the present invention (compound 55). The characteristics of the organic EL device thus fabricated were measured in an atmosphere at ordinary temperature. Table 1 summarizes the results of the emission characteristics measurements performed by applying a DC voltage to the organic EL device.

Comparative Example 1

For comparison, an organic EL device was fabricated under the same conditions used in Example 8, except that the material of the electron transport layer 5 used in Example 8 was changed to $Alq_3$. The characteristics of the organic EL device thus fabricated were measured in an atmosphere at ordinary temperature. Table 1 summarizes the results of the emission characteristics measurements performed by applying a DC voltage to the organic EL device.

Comparative Example 2

For comparison, an organic EL device was fabricated under the same conditions used in Example 8, except that the material of the electron transport layer 5 used in Example 8 was changed to the comparative compound 1. The characteristics of the organic EL device thus fabricated were measured in an atmosphere at ordinary temperature. Table 1 summarizes the results of the emission characteristics measurements performed by applying a DC voltage to the organic EL device.

Comparative Example 3

For comparison, an organic EL device was fabricated under the same conditions used in Example 8, except that the material of the electron transport layer 5 used in Example 8 was changed to the comparative compound 2. The characteristics of the organic EL device thus fabricated were measured in an atmosphere at ordinary temperature. Table 1 summarizes the results of the emission characteristics measurements performed by applying a DC voltage to the organic EL device.

Comparative Example 4

For comparison, an organic EL device was fabricated under the same conditions used in Example 8, except that the material of the electron transport layer 5 used in Example 8 was changed to the comparative compound 3. The characteristics of the organic EL device thus fabricated were measured in an atmosphere at ordinary temperature. Table 1 summarizes the results of the emission characteristics measurements performed by applying a DC voltage to the organic EL device.

TABLE 1

|  |  | Voltage [V] (@10 mA/$cm^2$) | Luminance [cd/$m^2$] (@10 mA/$cm^2$) | Current efficiency [cd/A] (@10 mA/$cm^2$) | Power efficiency [lm/W] (@10 mA/$cm^2$) |
|---|---|---|---|---|---|
| Ex. 8 | Compound 3 | 4.10 | 376 | 3.34 | 2.56 |
| Ex. 9 | Compound 11 | 4.40 | 335 | 3.41 | 2.43 |
| Ex. 10 | Compound 55 | 4.60 | 296 | 2.81 | 1.92 |
| Com. Ex. 1 | $Alq_3$ | 5.70 | 268 | 2.60 | 1.43 |

TABLE 1-continued

| | | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) |
|---|---|---|---|---|---|
| Com. Ex. 2 | Comparative compound 1 | 6.60 | 303 | 2.76 | 1.31 |
| Com. Ex. 3 | Comparative compound 2 | 7.50 | 263 | 2.63 | 1.10 |
| Com. Ex. 4 | Comparative compound 3 | 7.40 | 257 | 2.45 | 1.04 |

As can be seen in Table 1, the driving voltage at the current density of 10 mA/cm$^2$ was 4.10 V, 4.40 V, and 4.60 V in Examples 8, 9, and 10, respectively, greatly lower than 5.70 V of Comparative Example 1 in which Alq$_3$ was used, and 6.60 V to 7.50 V of Comparative Examples 2 to 4 in which the comparative compounds 1 to 3 were used. Further, the luminance, the current efficiency, and the power efficiency all greatly improved at the current density of 10 mA/cm$^2$.

Example 11

The glass substrate 1 having ITO (thickness 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less. This was followed by formation of the hole transport layer 3 by forming NPD over the transparent anode 2 in a thickness of 60 nm at a deposition rate of 2 Å/s. Then, the light emitting layer 4 was formed on the hole transport layer 3 in a thickness of 30 nm by the dual vapor deposition of 2-(tert-butyl)-9,10-diphenylanthracene (TBADN) and blue fluorescence emitter DPAVB at a deposition rate ratio of TBADN:DPAVB=95:5. The electron transport layer 5 was then formed on the light emitting layer 4 by forming the compound of Example 1 of the present invention (compound 3) in a thickness of 30 nm at a deposition rate of 2 Å/s. Then, the electron injection layer 6 was formed on the electron transport layer 5 by forming a magnesium silver alloy in a thickness of 100 nm at a deposition rate of 3.3 Å/s. Finally, the cathode 7 was formed by vapor depositing silver in a thickness of 10 nm. The characteristics of the organic EL device thus fabricated were measured in an atmosphere at ordinary temperature.

Table 2 summarizes the results of the emission characteristics measurements performed by applying a DC voltage to the organic EL device fabricated with the compound of Example 1 of the present invention (compound 3).

Comparative Example 5

For comparison, an organic EL device was fabricated under the same conditions used in Example 11, except that the material of the electron transport layer 5 used in Example 11 was changed to Alq$_3$. The characteristics of the organic EL device thus fabricated were measured in an atmosphere at ordinary temperature. Table 2 summarizes the results of the emission characteristics measurements performed by applying a DC voltage to the organic EL device.

TABLE 2

| | | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) |
|---|---|---|---|---|---|
| Ex. 11 | Compound 3 | 4.80 | 712 | 6.48 | 4.24 |
| Com. Ex. 5 | Alq$_3$ | 8.80 | 772 | 7.68 | 2.74 |

As can be seen in Table 2, the driving voltage at the current density of 10 mA/cm$^2$ was 4.80 V in Example 11, greatly lower than 8.80 V of Comparative Example 5 in which Alq$_3$ was used. Further, the power efficiency greatly improved at the current density of 10 mA/cm$^2$.

As is clear from these results, the organic EL devices using the compounds having a bipyridyl group and a triphenylene ring structure of the present invention can greatly improve power efficiency, and can achieve a considerably low actual driving voltage compared to the devices that use the common electron transport material Alq$_3$, and the devices that use the comparative compounds 1 to 3 having a non-planar central skeleton structure.

As demonstrated above, the organic EL devices using the compounds having a bipyridyl group and a triphenylene ring structure of the present invention have a considerably low driving voltage. The electron mobility of the compounds having a bipyridyl group and a triphenylene ring structure of the present invention is thus expected to be much faster than that of the common electron transport material Alq$_3$.

INDUSTRIAL APPLICABILITY

The compounds having a bipyridyl group and a triphenylene ring structure of the present invention have a desirable electron injection and transport performance and a stable thin-film state, and are desirable for organic EL devices. The organic EL device produced by using the compounds can have high efficiency and a low actual driving voltage, and can thus have improved durability. There are potential applications for, for example, home electronic appliances and illuminations.

DESCRIPTION OF REFERENCE NUMERALS AND SIGNS

1 Glass substrate
2 Transparent anode
3 Hole transport layer
4 Light emitting layer
5 Electron transport layer
6 Electron injection layer
7 Cathode

The invention claimed is:

1. An organic electroluminescent device comprising a pair of electrodes, and one or more organic layers sandwiched between the pair of electrodes, wherein a compound of the following general formula (2) having a substituted bipyridyl and triphenylene ring structure is used as constituent material of at least one of the organic layers, (2)

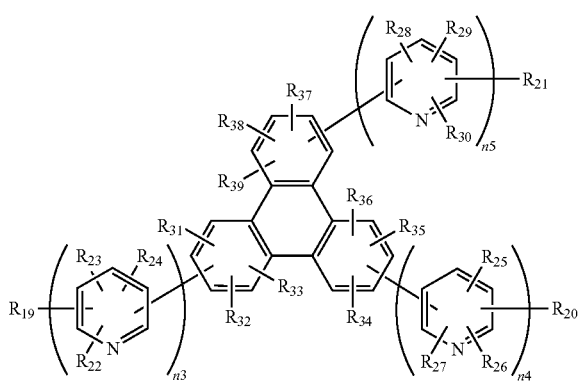

wherein $R_{19}$ to $R_{39}$ may be the same or different, and represent a hydrogen atom, a deuterium atom, a fluorine atom, a chlorine atom, cyano, trifluoromethyl, linear or branched alkyl of 1 to 6 carbon atoms that may have a substituent, a substituted or unsubstituted aromatic hydrocarbon group, a substituted or unsubstituted aromatic heterocyclic group, or a substituted or unsubstituted condensed polycyclic aromatic group, and wherein n3, n4, and n5 may be the same or different, and represent 2 or 3, and the plurality of $R_{22}$ to $R_{30}$ may be the same or different, respectively; and wherein when n3, n4 or n5 is 2, the bipyridyl bound to the triphenylene ring is 2,2'-bipyridyl or 2,4'-bipyzidyl.

2. The organic electroluminescent device according to claim 1, wherein the organic layer is an electron transport layer, and the compound represented by the general formula (2) is used as at least one of constituent materials in the electron transport layer.

3. The organic electroluminescent device according to claim 1, wherein the organic layer is an electron injection layer, and the compound represented by the general formula (2) is used as at least one of constituent materials in the electron injection layer.

4. The organic electroluminescent device according to claim 1, wherein the organic layer is a light emitting layer, and the compound represented by the general formula (2) is used as at least one of constituent materials in the light emitting layer.

* * * * *